(12) United States Patent
Kaiser et al.

(10) Patent No.: US 9,090,532 B2
(45) Date of Patent: Jul. 28, 2015

(54) ORGANIC ELECTROLUMINESCENT DEVICE

(75) Inventors: Joachim Kaiser, Darmstadt (DE); Horst Vestweber, Gilserberg-Winterscheid (DE); Simone Leu, Dittelsheim-Hessloch (DE); Arne Buesing, Frankfurt (DE); Holger Heil, Frankfurt (DE); Philipp Stoessel, Frankfurt (DE)

(73) Assignee: Merck Patent GmbH (DE)

( * ) Notice: Subject to any disclaimer, the term of this patent is extended or adjusted under 35 U.S.C. 154(b) by 570 days.

(21) Appl. No.: 13/001,823

(22) PCT Filed: May 22, 2009

(86) PCT No.: PCT/EP2009/003660
§ 371 (c)(1),
(2), (4) Date: Dec. 29, 2010

(87) PCT Pub. No.: WO2010/012330
PCT Pub. Date: Feb. 4, 2010

(65) Prior Publication Data
US 2011/0108821 A1    May 12, 2011

(30) Foreign Application Priority Data

Jul. 29, 2008  (DE) .................... 10 2008 035 413

(51) Int. Cl.
*H01L 51/50* (2006.01)
*C07C 13/62* (2006.01)
*C09K 11/06* (2006.01)
*H01L 51/00* (2006.01)

(52) U.S. Cl.
CPC ............. *C07C 13/62* (2013.01); *C09K 11/06* (2013.01); *H01L 51/0056* (2013.01); *H01L 51/0058* (2013.01); *C07C 2103/16* (2013.01); *C09K 2211/1007* (2013.01); *C09K 2211/1011* (2013.01); *H01L 51/5012* (2013.01); *H01L 51/5048* (2013.01); *Y02E 10/549* (2013.01)

(58) Field of Classification Search
USPC ................. 428/690, 917; 313/504, 505, 506; 257/40, E51.05, E51.026, E51.032; 585/27
See application file for complete search history.

(56) References Cited

U.S. PATENT DOCUMENTS

| 2004/0241491 A1 | 12/2004 | Hatwar |
| 2005/0074630 A1 | 4/2005 | Kanno et al. |
| 2007/0138947 A1 | 6/2007 | Popovic et al. |

(Continued)

FOREIGN PATENT DOCUMENTS

| JP | 2004311420 A | 11/2004 |
| JP | 2005-123205 A | 5/2005 |

(Continued)

OTHER PUBLICATIONS

Setayesh, et al., "Polyfluorenes with Polyphenylene Dendron Side Chains: Toward Non-Aggregating, Light-Emitting Polymers," *J. Am. Chem. Soc.*, vol. 123, pp. 946-953 (2001).

(Continued)

*Primary Examiner* — Gregory Clark
(74) *Attorney, Agent, or Firm* — Drinker Biddle & Reath LLP

(57) ABSTRACT

The present invention relates to white emitting organic electroluminescent devices having at least one blue fluorescent emitter layer.

17 Claims, 1 Drawing Sheet

Structure of the electroluminescent device according to the invention

(56) References Cited

U.S. PATENT DOCUMENTS

| | | | |
|---|---|---|---|
| 2007/0205412 A1* | 9/2007 | Bae et al. | 257/40 |
| 2009/0184313 A1* | 7/2009 | Buesing et al. | 257/40 |
| 2009/0261717 A1* | 10/2009 | Buesing et al. | 313/504 |
| 2010/0237323 A1 | 9/2010 | Akai et al. | |
| 2010/0314648 A1 | 12/2010 | Fehrer et al. | |

FOREIGN PATENT DOCUMENTS

| | | |
|---|---|---|
| JP | 2007-173827 A | 7/2007 |
| JP | 2009099545 A | 5/2009 |
| JP | 2010-541144 A | 12/2010 |
| WO | WO-2004/041901 A1 | 5/2004 |
| WO | WO-2007/140847 A1 | 12/2007 |
| WO | 2008006449 A1 | 1/2008 |

OTHER PUBLICATIONS

Chen et al., "Organic Electroluminescent Material and Device", Tsinghua University Press, pp. 219-233 (Jun. 30, 2007).

Chinese Office Action dated Aug. 28, 2014 for Chinese Patent Application No. 200980125133.9.

* cited by examiner

Figure 1: Structure of the electroluminescent device according to the invention
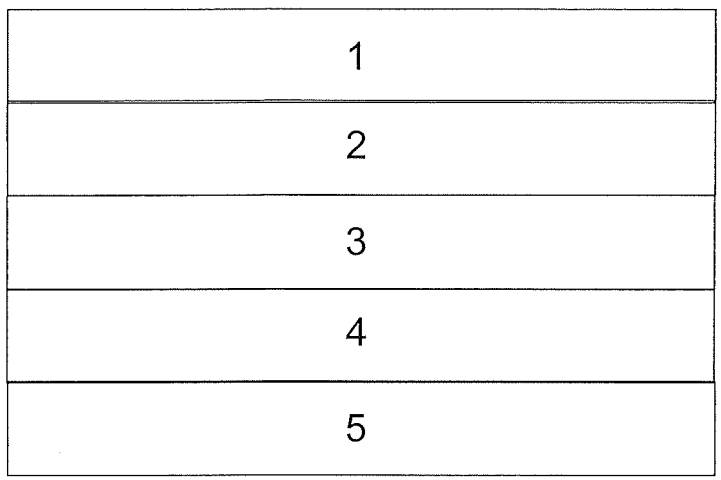

ORGANIC ELECTROLUMINESCENT DEVICE

RELATED APPLICATIONS

This application is a national stage application (under 35 U.S.C. §371) of PCT/EP2009/003660, filed May 22, 2009, which claims benefit of German Application No. 10 2008 035 413.9, filed Jul. 29, 2008.

The present invention relates to white-emitting organic electroluminescent devices which comprise dopants having certain physical properties in the blue-emitting layer.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO98/27136. A development in the area of organic electroluminescent devices are white-emitting OLEDs. These can be employed either for monochromically white displays or with coloured filters for full-colour displays. Furthermore, they are suitable for lighting applications. White-emitting organic electroluminescent devices based on low-molecular-weight compounds generally have at least two emission layers. They frequently have at least three emission layers which exhibit blue, green and orange or red emission. Either fluorescent or phosphorescent emitters are used in the emission layers, where the phosphorescent emitters exhibit significant advantages owing to the higher achievable efficiency. The general structure of white-emitting OLEDs of this type having at least one phosphorescent layer is described, for example, in WO 05/011013. Owing to the higher achievable efficiency, white-emitting OLEDs which comprise only phosphorescent emitter layers would be desirable. However, since blue-phosphorescent emitters generally still do not meet the standard requirements, in particular with respect to the operating lifetime, hybrid OLEDs, i.e. a fluorescent blue emitter layer combined with phosphorescent orange or red and green emitter layers (in the case of three-colour white) or a fluorescent blue emitter layer combined with a phosphorescent yellow to orange emitter layer (in the case of two-colour white), are used in most applications in accordance with the prior art. The blue-emitting layer here is frequently arranged on the cathode side.

A basic problem of OLEDs of this type consists in that the blue emission layer arranged on the cathode side sees a particularly electron-rich environment. The blue dopants used in accordance with the prior art are generally arylamines containing condensed aromatic rings, for example chrysenamines or pyrenamines, which frequently have a stability problem with respect to electrons, which results in a reduction in the lifetime. The lifetime of the blue emitter is therefore limiting for the lifetime of the white-emitting electroluminescent device. There is therefore a need for improvement here. In particular, the aim was to find blue-emitting dopants which have high stability to an electron-rich environment and thus result in an improved lifetime of the white-emitting device.

Surprisingly, it has been found that a white-emitting organic electroluminescent device in which the blue-emitting layer is arranged on the cathode side has a significantly improved lifetime if the blue-emitting dopant used is a compound whose HOMO (highest occupied molecular orbital) is less than −5.2 eV.

The invention thus relates to an organic electroluminescent device comprising, in this sequence, an anode, a first emitter layer, a second emitter layer which is a blue-emitting layer, where the blue-emitting layer comprises a host material in a proportion of 90-99.9% by vol. and a dopant in a proportion of 0.1-10% by vol., and a cathode, characterised in that the dopant has an HOMO of less than −5.2 eV.

The HOMO is determined as described in general terms below in Example 1.

A preferred embodiment of the invention relates to a white-emitting organic electroluminescent device. This is characterised in that it emits light having CIE colour coordinates in the range from 0.28/0.29 to 0.45/0.41.

The organic electroluminescent device according to the invention comprises, as described above, anode, cathode and at least two emitting layers which are arranged between the anode and the cathode. The organic electroluminescent device does not necessarily have to comprise only layers built up from organic or organometallic materials. Thus, it is also possible for the anode, cathode and/or one or more layers to comprise inorganic materials or to be built up entirely from inorganic materials.

If the organic electroluminescent device has precisely two emitting layers, the first emitter layer, i.e. the emitter layer on the anode side, is preferably a yellow- or orange-emitting emitter layer, preferably a phosphorescent emitter layer.

In a preferred embodiment of the invention, the electroluminescent device according to the invention has at least three emitting layers.

If the organic electroluminescent device has three emitting layers, one of these layers is preferably a red- or orange-emitting emitter layer and one of the layers is a green-emitting emitter layer. In a preferred embodiment of the invention, the red- or orange-emitting layer is on the anode side and the green-emitting layer lies between the red-emitting layer and the blue-emitting layer. In a preferred embodiment of the invention, the red- or orange-emitting layer and/or the green-emitting layer are phosphorescent layers. Both the red- or orange-emitting layer and the green-emitting layer are particularly preferably phosphorescent layers.

It is also possible for the organic electroluminescent device to have more than three emitter layers.

In a preferred embodiment of the invention, no further emitting layer is present between the blue-emitting layer and the cathode.

In a preferred embodiment of the invention, the blue-emitting layer is a fluorescent layer, i.e. the dopant is a fluorescent dopant.

A yellow-emitting layer is taken to mean a layer whose photoluminescence maximum is in the range from 540 to 570 nm. An orange-emitting layer is taken to mean a layer whose photoluminescence maximum is in the range from 570 to 600 nm. A red-emitting layer is taken to mean a layer whose photoluminescence maximum is in the range from 600 to 750 nm. A green-emitting layer is taken to mean a layer whose photoluminescence maximum is in the range from 490 to 540 nm. A blue-emitting layer is taken to mean a layer whose photoluminescence maximum is in the range from 440 to 490 nm. The photoluminescence maximum is determined by measurement of the photoluminescence spectrum of the layer having a layer thickness of 50 nm.

The organic electroluminescent device according to the invention particularly preferably has the following structure: anode/orange- or red-phosphorescent emitter layer/green-phosphorescent emitter layer/blue-fluorescent emitter layer/cathode. The electroluminescent device may also have further layers which are not mentioned above.

This general device structure is shown diagrammatically in FIG. 1. Layer 1 here stands for the anode, layer 2 for the red-phosphorescent emitter layer, layer 3 for the green-phosphorescent emitter layer, layer 4 for the blue-fluorescent emitter layer and layer 5 for the cathode. The electroluminescent device may also have further layers which are not depicted in FIG. 1.

For the purposes of this invention, a phosphorescent compound, as present in the phosphorescent emitter layers in the organic electroluminecent device according to the invention, is a compound which exhibits luminescence from an excited state of relatively high spin multiplicity, i.e. a spin state >1, in particular from an excited triplet state, at room temperature. For the purposes of this invention, all luminescent transition-metal complexes from the second and third transition-metal series, in particular all luminescent iridium and platinum compounds, are to be regarded as phosphorescent compounds.

For the purposes of this invention, a fluorescent compound, as present in the blue-fluorescent emitter layer, is a compound which exhibits luminescence from an excited singlet state at room temperature. For the purposes of this invention, all luminescent compounds which are built up only from the elements C, H, N, O, S, F, B and P are, in particular, to be regarded as fluorescent compounds.

The blue-emitting dopant present in the blue-emitting emitter layer is described in greater detail below:

As described above, the blue dopant has an HOMO (highest occupied molecular orbital) of less than −5.2 eV. The HOMO is preferably less than −5.3 eV, particularly preferably less than −5.4 eV.

The blue dopant furthermore preferably has an LUMO (lowest unoccupied molecular orbital) of less than −2.3 eV, particularly preferably less than −2.5 eV. The LUMO is determined as described in general terms below in Example 1.

As described above, the blue dopant is present in the blue-emitting layer in a concentration of 0.1-10% by vol. A proportion of 0.2-7% by vol. is preferred, a proportion of 0.5-5% by vol. is particularly preferred, a proportion of 0.8-3% by vol. is very particularly preferred.

In a preferred embodiment of the invention, the blue dopant contains no diarylamino groups, particularly preferably no amino groups at all. This preference is due to the comparatively low stability of diarylamino groups to electrons.

In a preferred embodiment of the invention, the blue dopant is a compound of the following formula (1):

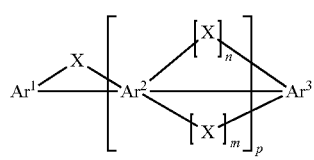

formula (1)

where the following applies to the symbols and indices used:

$Ar^1, Ar^2, Ar^3$ are on each occurrence, identically or differently, an aryl or heteroaryl group having 5 to 30 aromatic ring atoms, which may be substituted by one or more radicals $R^1$;

X is on each occurrence, identically or differently, a group selected from $BR^2$, $C(R^2)_2$, $Si(R^2)_2$, C=O, C=NR$^2$, C=C(R$^2$)$_2$, O, S, S=O, SO$_2$, NR$^2$, PR$^2$, P(=O)R$^2$ or P(=S)R$^2$;

$R^1, R^2$ are on each occurrence, identically or differently, H, D, F, Cl, Br, I, C(=O)Ar$^4$, P(=O)(Ar$^4$)$_2$, S(=O)Ar$^4$, S(=O)$_2$Ar$^4$, CR$^2$=CR$^2$Ar$^4$, CHO, CR$^3$=C(R$^3$)$_2$, CN, NO$_2$, Si(R$^3$)$_3$, B(OR$^3$)$_2$, B(R$^3$)$_2$, B(N(R$^3$)$_2$)$_2$, OSO$_2$R$^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R$^3$, where in each case one or more non-adjacent CH$_2$ groups may be replaced by R$^3$C=CR$^3$, C≡C, Si(R$^3$)$_2$, Ge(R$^3$)$_2$, Sn(R$^3$)$_2$, C=O, C=S, C=Se, C=NR$^3$, P(=O)R$^3$, SO, SO$_2$, NR$^3$, O, S or CONR$^3$ and where one or more H atoms may be replaced by F, Cl, Br, I, CN or NO$_2$, or an aromatic or heteroaromatic ring system having 5 to 60 aromatic ring atoms, which may in each case be substituted by one or more radicals R$^3$, or a combination of these systems; two or more substituents R$^1$ and R$^2$ here may also form a mono- or polycyclic, aliphatic or aromatic ring system with one another;

$R^3$ is on each occurrence, identically or differently, H, D or an aliphatic or aromatic hydrocarbon radical having 1 to 20 C atoms;

$Ar^4$ is on each occurrence, identically or differently, an aromatic or heteroaromatic ring system having 5-30 aromatic ring atoms, which may be substituted by one or more non-aromatic radicals R$^1$; two radicals Ar on the same nitrogen or phosphorus atom may also be linked to one another here by a single bond or a bridge X;

m, n are 0 or 1, with the proviso that m+n=1;

p is 1, 2, 3, 4, 5 or 6;

$Ar^1, Ar^2$ and X together form a five-membered ring or a six-membered ring, and $Ar^2, Ar^3$ and X together form a five-membered ring or a six-membered ring.

The sum of all π electrons in groups $Ar^1, Ar^2$ and $Ar^3$ is preferably at least 28 if p=1 and at least 34 if p=2 and at least 40 if p=3 and at least 46 if p=4 and at least 52 if p=5 and at least 58 if p=6.

The determination of the sum of all π electrons in groups $Ar^1, Ar^2$ and $Ar^3$ is obvious to the person skilled in the art. Thus, each double bond in an aryl group (where the double bonds are delocalised) stands for two π electrons, meaning that, for example, benzene has 6 π electrons, naphthalene has 10 π electrons, anthracene and phenanthrene have 14 π electrons, pyrene has 16 π electrons, naphthacene, benzanthracene and chrysene have 18 π electrons, and perylene has 20 π electrons. In an aryl group, the number of π electrons corresponds to the number of C atoms in the aromatic ring system. In heteroaromatic compounds, each double bond (the double bonds here are again delocalised) also contributes two π electrons, where these delocalised double bonds can be formed either between two carbon atoms, between carbon and nitrogen or between two nitrogen atoms. Furthermore, in five-membered heteroaryl groups, the heteroatom, which is formally not bonded in a double bond (i.e., for example, the nitrogen in pyrrole, the oxygen in furan or the sulfur in thiophene), likewise in each case contributes two π electrons to the overall π-electron system via the free electron pair. For example, pyridine, pyrazine, pyrimidine and pyridazine therefore each have 6 π electrons, quinoline and isoquinoline have 10 π electrons, phenanthroline has 14 π electrons, pyrrole, imidazole, pyrazole, thiophene, thiazole and furan each have 6 π electrons, indole, benzimidazole, benzothiophene and benzofuran each have 10 π electrons, and carbazole, dibenzothiophene and dibenzofuran each have 14 π electrons.

For the purposes of this invention, an aryl group or heteroaryl group is taken to mean an aromatic group or heteroaromatic group respectively having a common aromatic electron system, where an aryl group contains 6 to 30 C atoms and a heteroaryl group contains 2 to 30 C atoms and a total of at least 5 aromatic ring atoms. The heteroatoms are preferably selected from N, O and/or S. For the purposes of this invention, this can be a single homo- or heterocyclic ring, for example benzene, pyridine, thiophene, etc., or it can be a condensed aryl or heteroaryl group in which at least two aromatic or heteroaromatic rings, for example benzene rings, are fused to one another, i.e. are condensed onto one another by anellation, i.e. have at least one common edge and thus also a common aromatic system. This aryl or heteroaryl group may be substituted or unsubstituted; any substituents present may likewise form further ring systems. Thus, for example, systems such as naphthalene, anthracene, phenanthrene, pyrene, etc., are to be regarded as aryl groups for the purposes of this invention and quinoline, acridine, benzothiophene, carbazole, etc., are to be regarded as heteroaryl groups for the purposes of this invention, while, for example, biphenyl, fluorene, spirobifluorene, etc., are not aryl groups since separate aromatic electron systems are present here.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the total number of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but in which, in addition, a plurality of aryl or heteroaryl groups may be interrupted by a short, non-aromatic unit (less than 10% of the atoms other than H, preferably less than 5% of the atoms other than H), such as, for example, a C, N or O atom. Thus, for example, systems such as 9,9'-spirobifluorene, 9,9-diarylfluorene, triarylamine, diaryl ether, etc., are also to be regarded as aromatic ring systems for the purposes of this invention.

For the purposes of the present invention, a $C_1$- to $C_{40}$-alkyl group, in which individual H atoms or $CH_2$ groups may also be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. A $C_1$- to $C_{40}$-alkoxy group is particularly preferably taken to mean methoxy, ethoxy, n-propoxy, i-propoxy, n-butoxy, i-butoxy, s-butoxy, t-butoxy or 2-methylbutoxy. A $C_2$-$C_{24}$-aryl or -heteroaryl group, which can be monovalent or divalent depending on the use, may in each case also be substituted by the above-mentioned radicals $R^1$ and may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, benzofluoranthene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. In addition to the above-mentioned aryl and heteroaryl groups, aromatic and heteroaromatic ring systems are, for the purposes of this invention, taken to mean, in particular, biphenylene, terphenylene, fluorene, benzofluorene, dibenzofluorene, spirobifluorene, dihydrophenanthrene, tetrahydropyrene, cis- or trans-indenofluorene, cis- or trans-monobenzoindenofluorene or cis- or trans-dibenzoindenofluorene.

In a preferred embodiment of the invention, the index p=1, 2 or 3, particularly preferably 1 or 2, very particularly preferably 1.

In a preferred embodiment of the invention, the sum of all π electrons in groups $Ar^1$, $Ar^2$ and $Ar^3$ is between 28 and 50, particularly preferably between 28 and 46, very particularly preferably between 28 and 42, in particular between 28 and 36, if p=1, and is between 34 and 56, particularly preferably between 34 and 52, very particularly preferably between 34 and 48, in particular between 34 and 40, if p=2, and is between 40 and 62, particularly preferably between 40 and 58, very particularly preferably between 40 and 54, in particular between 40 and 46, if p=3.

Preference is furthermore given to compounds of the formula (1) in which the symbols $Ar^1$, $Ar^2$ and $Ar^3$ stand, identically or differently on each occurrence, for an aryl or heteroaryl group having 5 to 22 aromatic ring atoms, in particular having 5 to 18 aromatic ring atoms. The groups $Ar^1$, $Ar^2$ and $Ar^3$ here are particularly preferably selected, independently of one another, from the group consisting of benzene, naphthalene, anthracene, phenanthrene, fluoranthene, naphthacene, benzanthracene, chrysene, pyrene, benzofluoranthene, triphenylene, perylene, dibenzanthracene, benzopyrene, picene, pentacene, pentaphene, benzophenanthrene, pyridine, pyrazine, pyrimidine, pyridazine, quinoline, isoquinoline, phenanthroline, acridine. The symbols $Ar^1$, $Ar^2$ and $Ar^3$ particularly preferably stand on each occurrence, identically or differently, for an aryl group having 6 to 18 aromatic ring atoms, in particular selected from benzene, naphthalene, anthracene, phenanthrene, fluoranthene, naphthacene, benzanthracene, chrysene, pyrene, benzofluoranthene and triphenylene.

Particularly preferred groups $Ar^1$ and $Ar^3$ which form a five-membered ring with $Ar^2$ are the groups of the formulae (2) to (85) shown below, each of which may be substituted by one or more radicals $R^1$. The symbol * stands for the position of the link from $Ar^1$ or $Ar^3$ to $Ar^2$, and the symbol # stands for the position of the link from $Ar^1$ or $Ar^3$ to X.

formula (2)

formula (3)

-continued
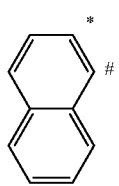
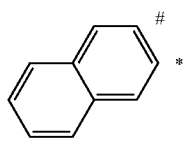
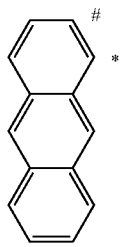
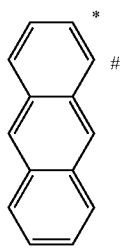
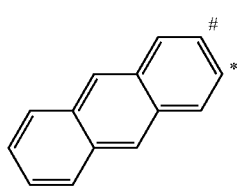
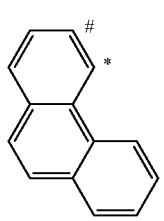
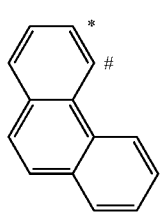
-continued
formula (4)
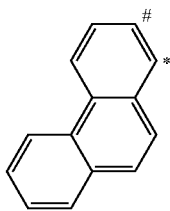
formula (5)
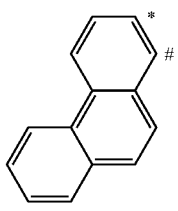
formula (6)
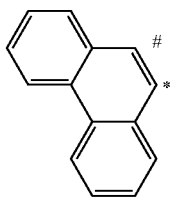
formula (7)
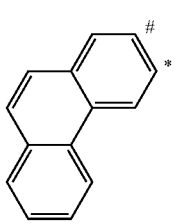
formula (8)
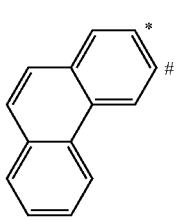
formula (9)
formula (10)
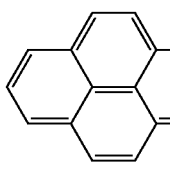
formula (11)
formula (12)
formula (13)
formula (14)
formula (15)
formula (16)
formula (17)
formula (18)

-continued
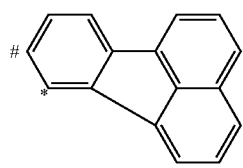
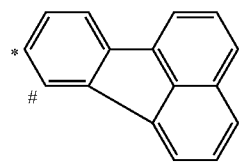
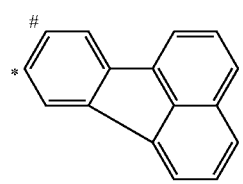
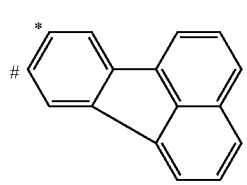
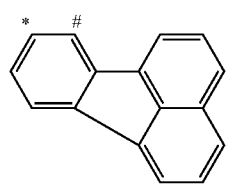
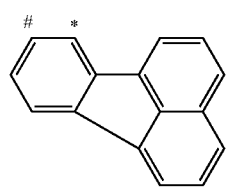
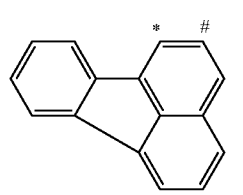
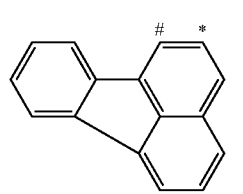
-continued
formula (19)
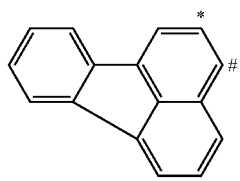
formula (20)
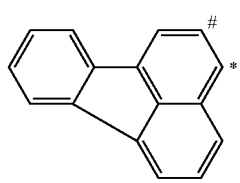
formula (21)
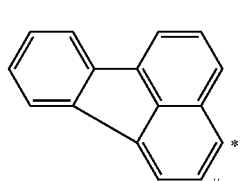
formula (22)
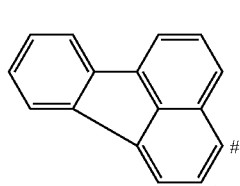
formula (23)
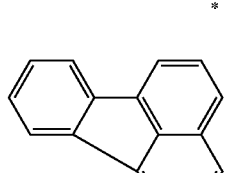
formula (24)
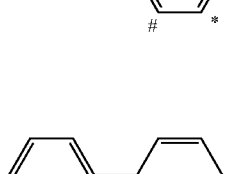
formula (25)
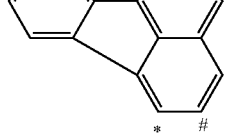
formula (26)
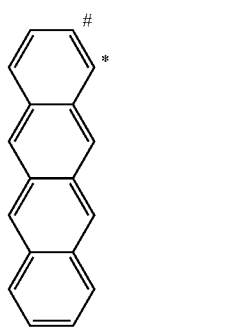
formula (27)
formula (28)
formula (29)
formula (30)
formula (31)
formula (32)
formula (33)

-continued
formula (34)
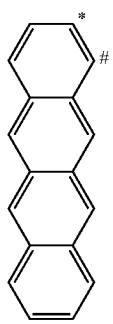
formula (35)
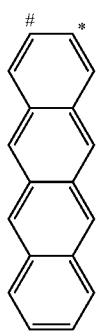
formula (36)
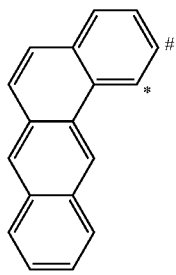
formula (37)
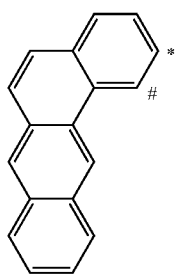
formula (38)
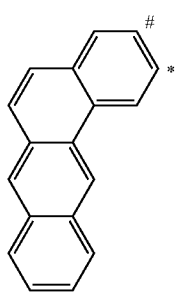
formula (39)
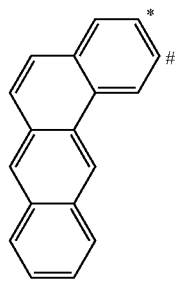
formula (40)
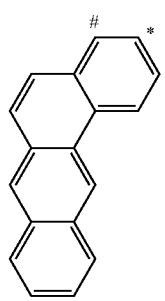
formula (41)
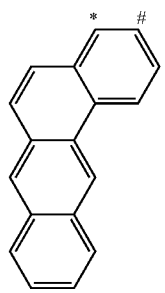
formula (42)
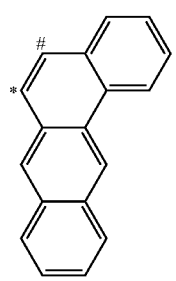
formula (43)
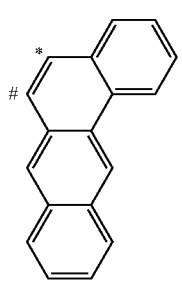

-continued
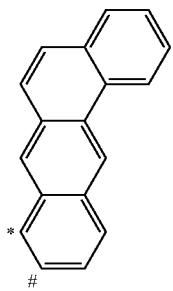
formula (44)
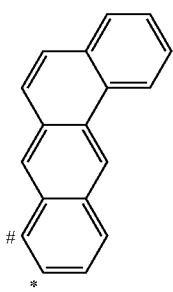
formula (45)
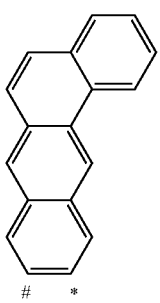
formula (46)
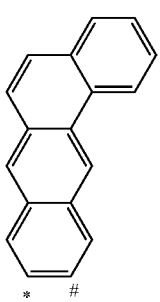
formula (47)
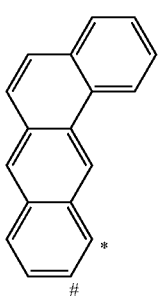
formula (48)
-continued
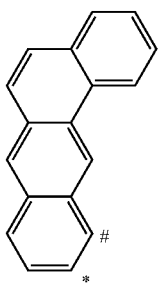
formula (49)
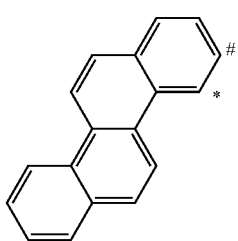
formula (50)
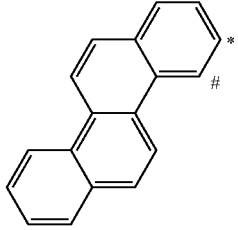
formula (51)
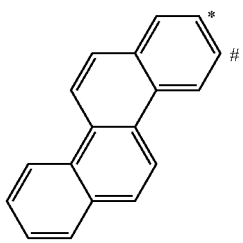
formula (52)
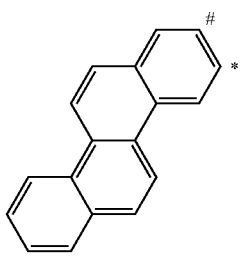
formula (53)
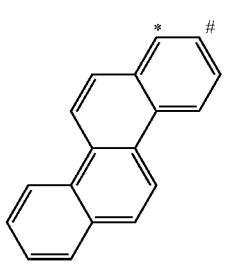
formula (54)

formula (55)
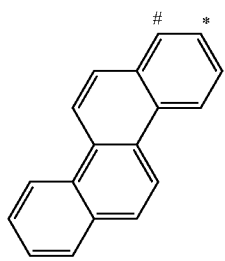
formula (56)
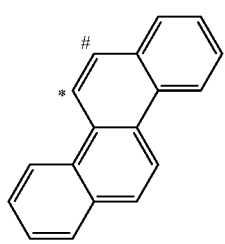
formula (57)
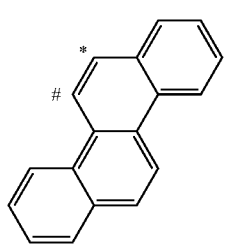
formula (58)
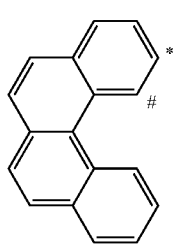
formula (59)
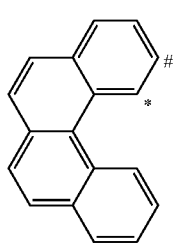
formula (60)
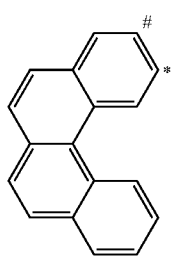
formula (61)
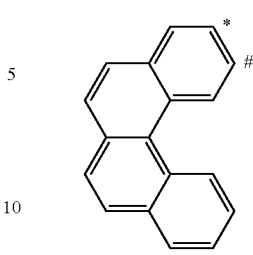
formula (62)
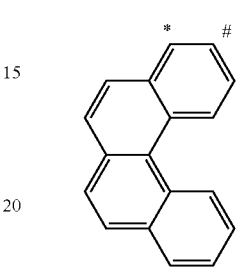
formula (63)
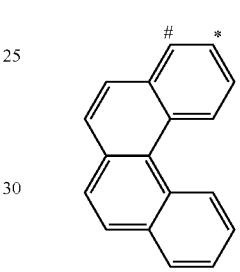
formula (64)
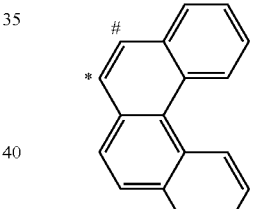
formula (65)
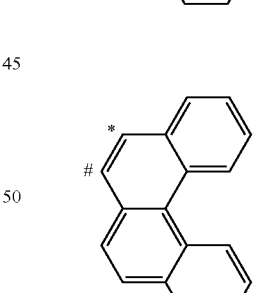
formula (66)
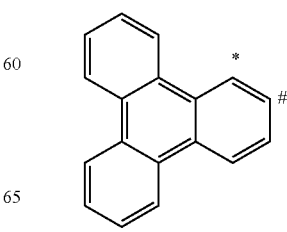

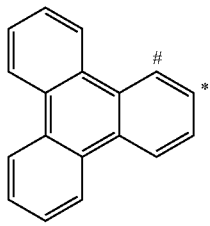
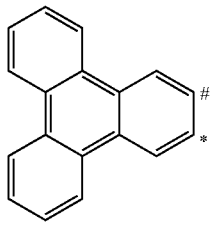
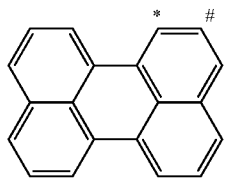
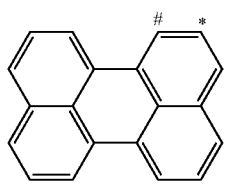
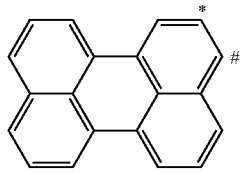
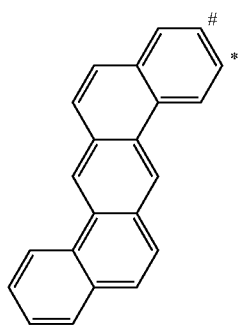
formula (67)
formula (68)
formula (69)
formula (70)
formula (71)
formula (72)
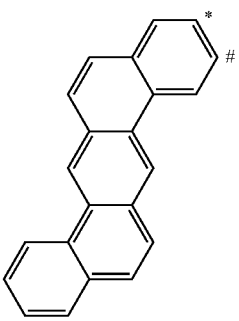
formula (73)
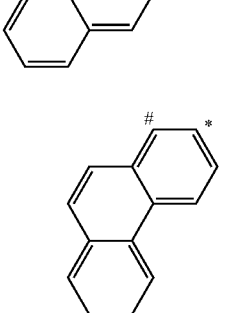
formula (74)
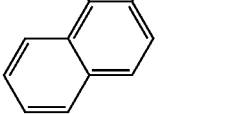
formula (75)
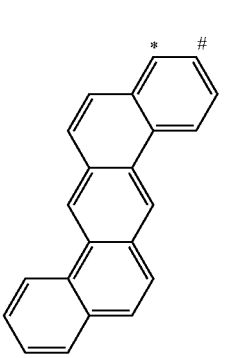
formula (76)
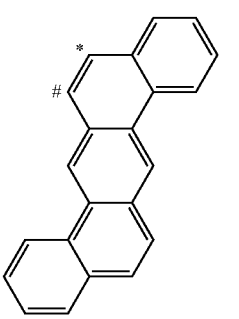
formula (77)
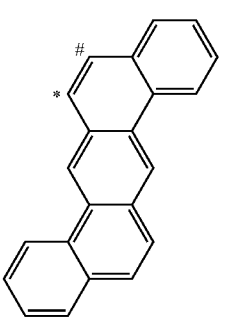

formula (78)
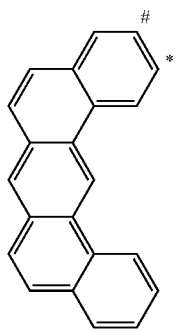
formula (79)
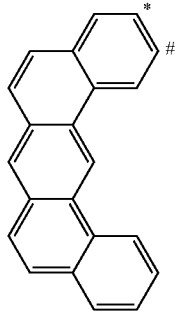
formula (80)
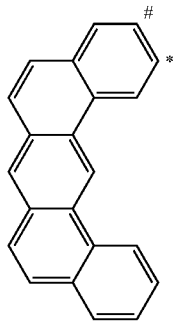
formula (81)
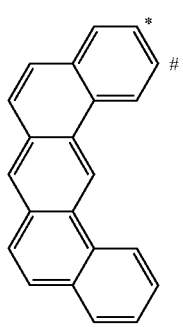
formula (82)
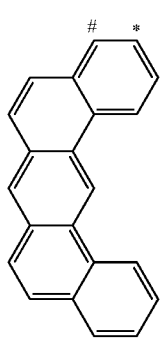
formula (83)
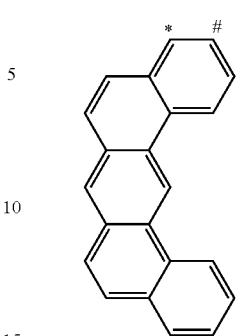
formula (84)
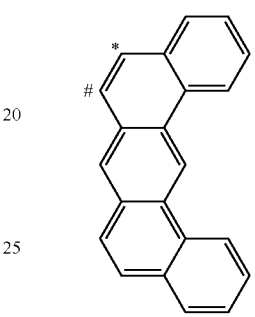
formula (85)
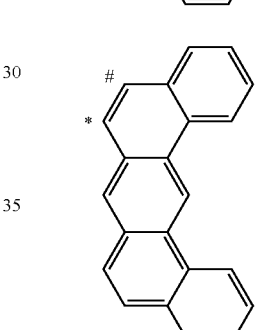
Particularly preferred groups Ar² are the groups of the formulae (86) to (110) shown below, each of which may be substituted by one or more radicals R¹. The symbol * stands for the position of the link from Ar² to Ar¹ or Ar³, and the symbol # stands for the position of the link from Ar² to X.
formula (86)
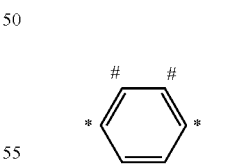
formula (87)
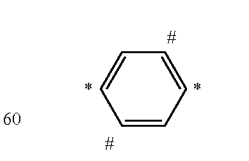
formula (88)
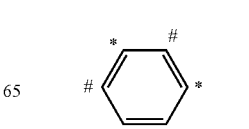

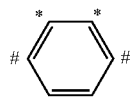
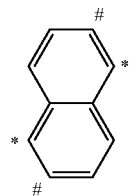
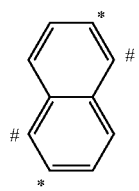
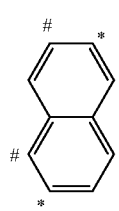
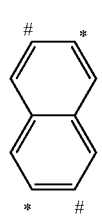
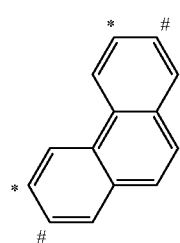
formula (89)
formula (90)
formula (91)
formula (92)
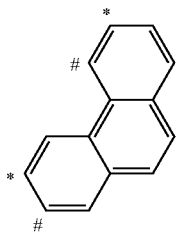
formula (93)
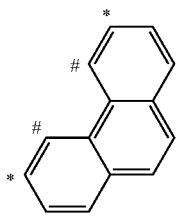
formula (94)
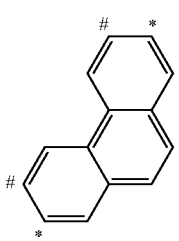
formula (95)
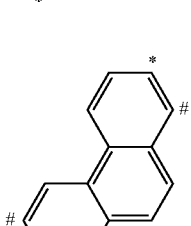
formula (96)
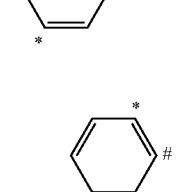
formula (97)
formula (98)
formula (99)
formula (100)
formula (101)
formula (102)
formula (103)

formula (104)
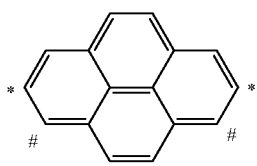

formula (105)
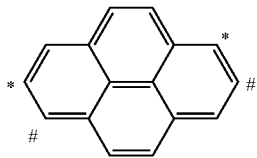

formula (106)
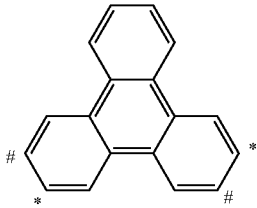

formula (107)
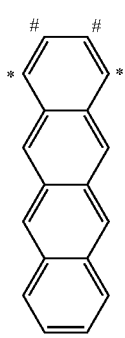

formula (108)
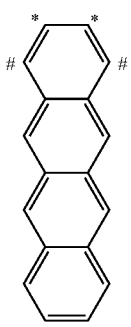

formula (109)
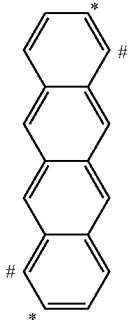

formula (110)

The formation of six-membered rings from two of the formulae depicted above and the group X is possible analogously.

Preference is furthermore given to compounds in which at least one of the groups $Ar^1$, $Ar^2$ and $Ar^3$ has at least 3 condensed rings, i.e. at least 14 π electrons, where these groups are preferably selected from the formulae depicted above. Particularly preferably, at least one of the groups $Ar^1$, $Ar^2$ and $Ar^3$ has at least 4 condensed rings, i.e. at least 16 π electrons. Very particularly preferably, at least one of the groups $Ar^1$, $Ar^2$ and $Ar^3$ has at least 4 condensed rings, i.e. at least 16 π electrons, and at least one of the other two groups $Ar^1$, $Ar^2$ and $Ar^3$ has at least 2 condensed rings, i.e. at least 10 π electrons.

Preference is furthermore given to compounds of the formula (1) in which the symbol X is selected, identically or differently on each occurrence, from the group consisting of $B(R^2)$, $C(R^2)_2$, $Si(R^2)_2$, O, S or $N(R^2)$, particularly preferably $C(R^2)_2$, S or $N(R^2)$. Very particularly preferably, all symbols X stand, identically or differently on each occurrence, for $C(R^2)_2$. $R^2$ here preferably stands for an alkyl or aryl group, as defined above.

Particularly preferably, $Ar^1$, $Ar^2$ and $Ar^3$ are selected from the formulae mentioned above and X simultaneously stands, identically or differently on each occurrence, for $C(R^2)_2$. $R^2$ here preferably stands for an alkyl or aryl group.

Particular preference is given to compounds of the formula (1) selected from the formulae (111) to (141), where the aromatic systems may each also be substituted by one or more radicals $R^1$:

formula (111)
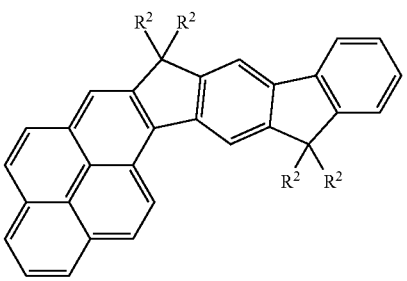

formula (112)
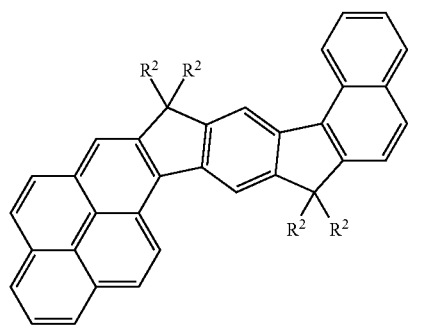
formula (113)
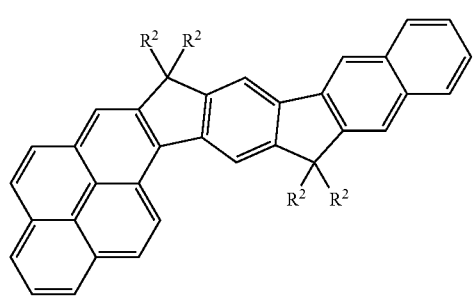
formula (114)
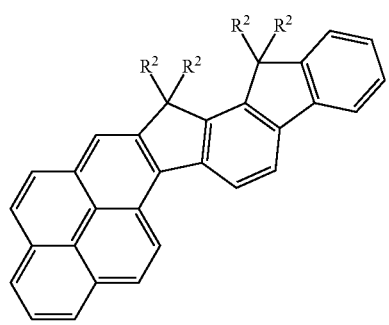
formula (115)
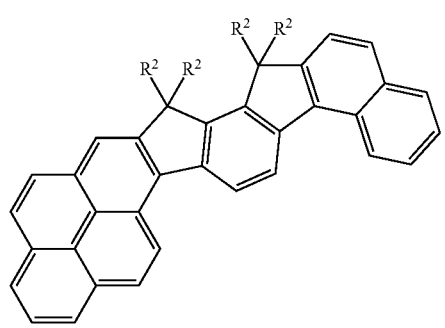
formula (116)
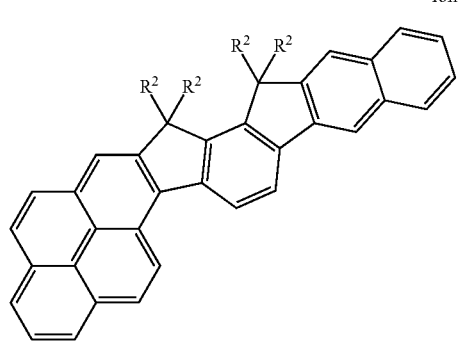
formula (117)
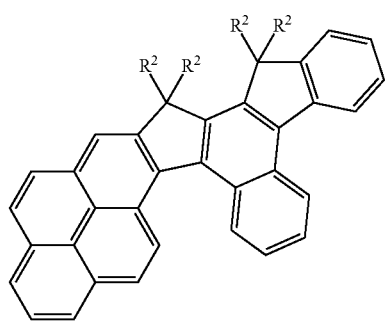
formula (118)
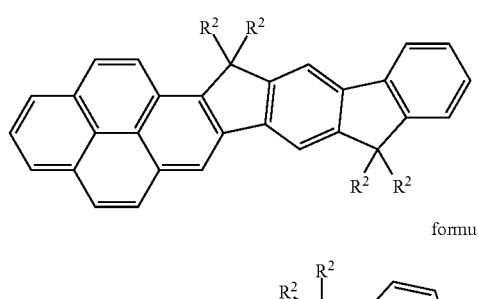
formula (119)
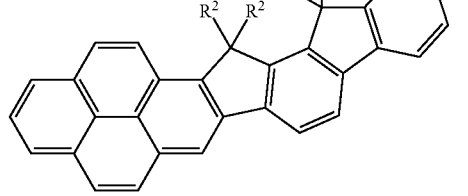
formula (120)
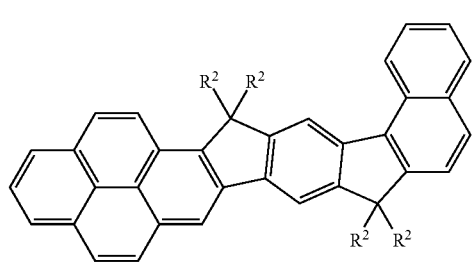
formula (121)
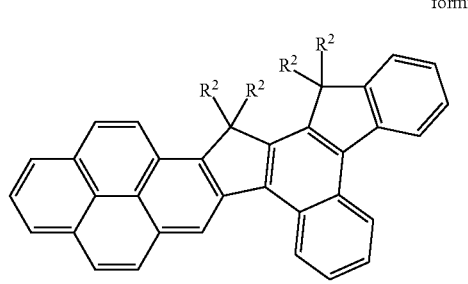
formula (122)
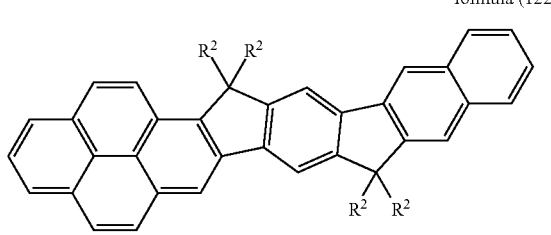

formula (123)
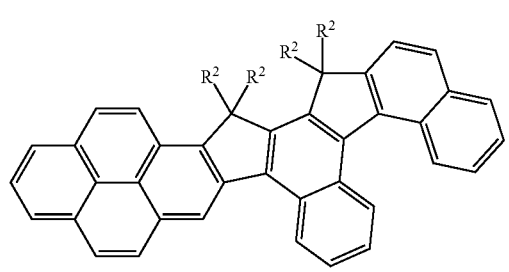
formula (124)
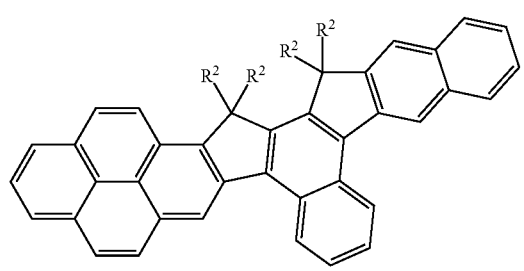
formula (125)
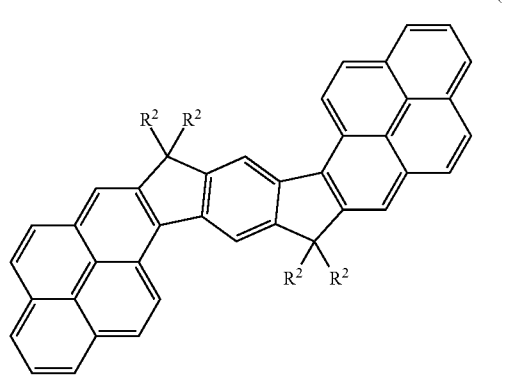
formula (126)
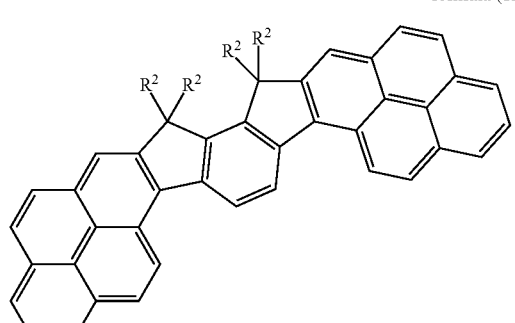
formula (127)
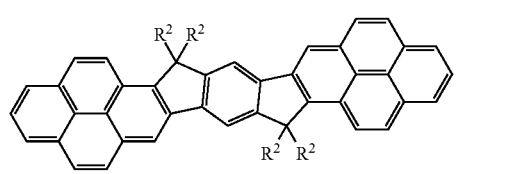
formula (128)
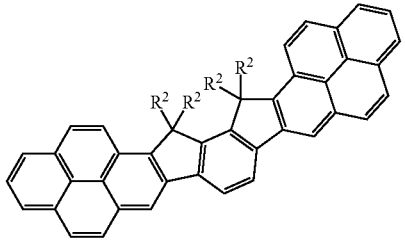
formula (129)
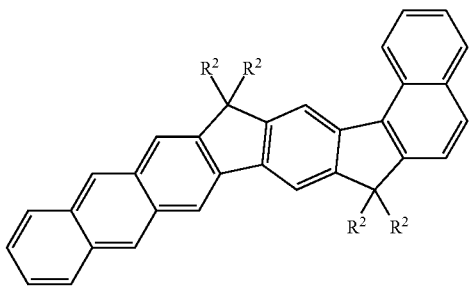
formula (130)
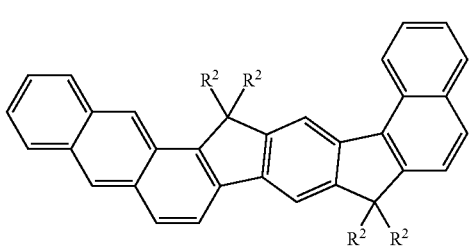
formula (131)
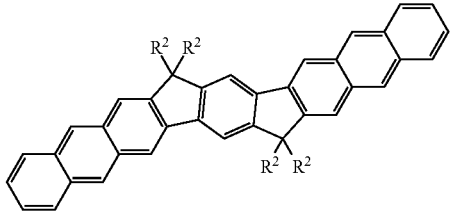
formula (132)
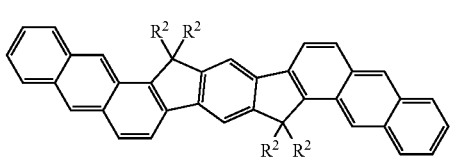
formula (133)
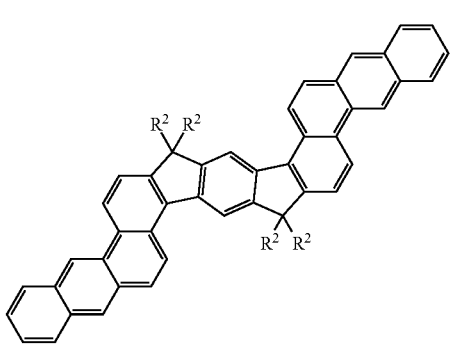

-continued formula (134)
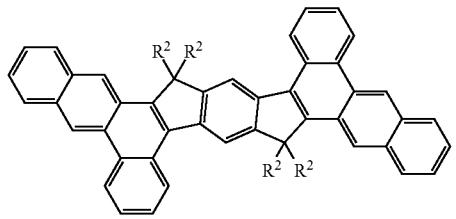

formula (135)
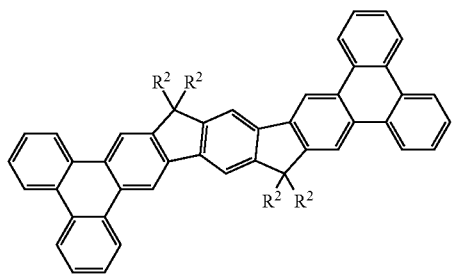

formula (136)
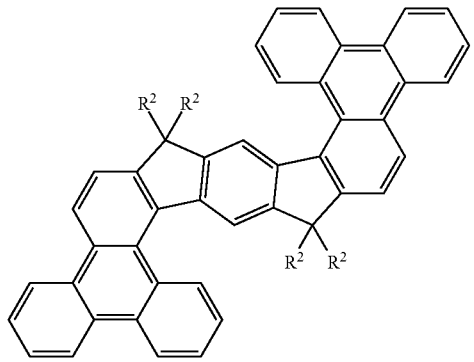

formula (137)
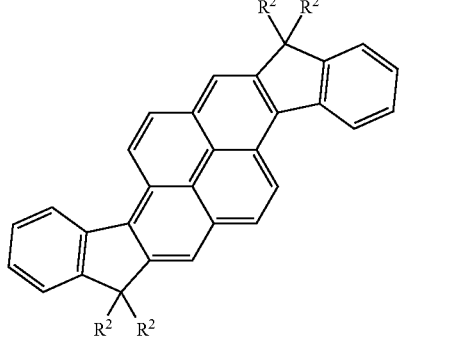

formula (138)
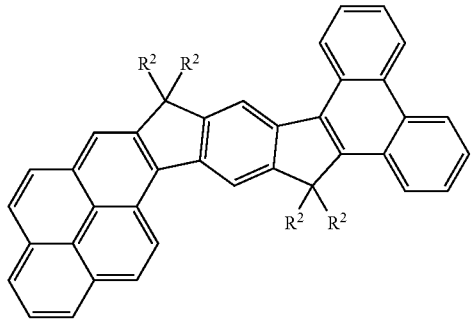

-continued formula (139)
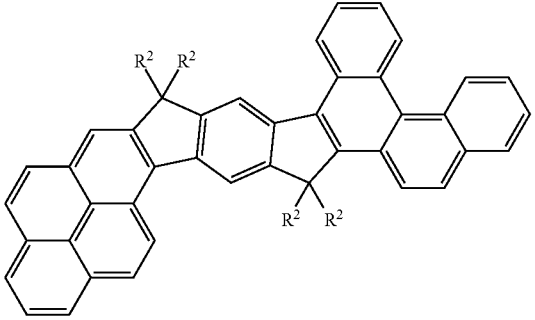

formula (140)
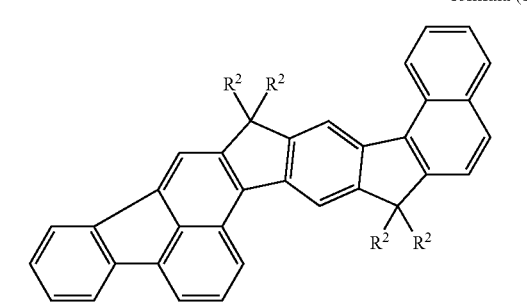

formula (141)
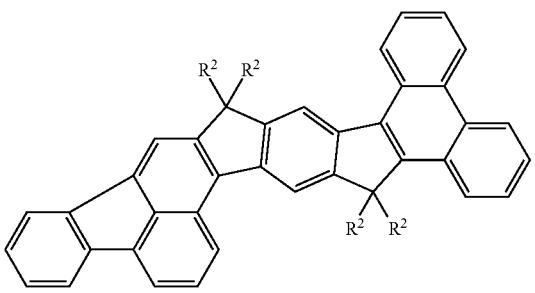

Preference is furthermore given to compounds of the formula (1) in which the symbol $R^1$, which may be bonded to $Ar^1$, $Ar^2$ or $Ar^3$ as a substituent, is selected on each occurrence, identically or differently, from the group consisting of H, D, F, $Si(R^3)_3$, straight-chain alkyl or alkoxy groups having 1 to 10 C atoms or branched or cyclic alkyl or alkoxy groups having 3 to 10 C atoms, each of which may be substituted by one or more radicals $R^3$, where in each case one or more non-adjacent $CH_2$ groups may be replaced by $R^3C=CR^3$ or O and where one or more H atoms may be replaced by F, or aromatic or heteroaromatic ring systems having 5 to 40 aromatic ring atoms, or a combination of these systems; two or more substituents $R^1$ here may also form a mono- or polycyclic, aliphatic or aromatic ring system with one another. The substituent $R^1$ is particularly preferably selected from H, D, straight-chain alkyl groups having 1 to 6 C atoms, branched or cyclic alkyl groups having 3 to 6 C atoms or an aromatic or heteroaromatic ring system having 5 to 24 aromatic ring atoms; two or more substituents $R^1$ here may also form a mono- or polycyclic ring system with one another. The substituent $R^1$ is very particularly preferably selected from H, D, alkyl groups selected from the group consisting of methyl, ethyl, n-propyl, isopropyl, n-butyl, isobutyl, tert-butyl, cyclopentyl or cyclohexyl, in particular methyl or tert-butyl, and aromatic or heteroaromatic ring systems selected from the group consisting of unsubstituted or $R^3$-substituted phenyl or naphthyl, benzimidazole, which may also be substituted by phenyl or other radicals $R^3$, phenylbenzimidazole, where the benzimidazole may also be substituted by phenyl or other radicals $R^3$, or triazine, which may also be substituted by phenyl or other radicals $R^3$. $R^1$ is very particularly preferably selected, identically or differently on each occurrence, from H or D.

Preference is furthermore given to compounds of the formula (1) in which the symbol $R^2$, which is bonded to the group X, is selected on each occurrence, identically or differently, from H, straight-chain alkyl groups having 1 to 10 C atoms or branched or cyclic alkyl groups having 3 to 10 C atoms, where in each case one or more non-adjacent $CH_2$ groups may be replaced by $-R^2C=CR^2-$ or $-O-$ and where one or more H atoms may be replaced by F, or a monovalent aryl or heteroaryl group having 5 to 16 aromatic ring atoms, which may be substituted by one or more non-aromatic radicals $R^2$; two radicals $R^2$ which are bonded in the same group X here may also form a ring system with one another. The radicals $R^2$ are particularly preferably selected from straight-chain alkyl groups having 1 to 4 C atoms or branched alkyl groups having 3 or 4 C atoms, in particular methyl groups, or phenyl groups; two or more radicals $R^2$ here may form a ring system with one another. If a plurality of radicals $R^2$ form a ring system with one another, a spiro structure is thereby formed. This may be preferred, in particular, if the radicals $R^2$ stand for phenyl groups or if two radicals $R^2$ stand for alkyl groups which form a ring system with one another.

Examples of preferred compounds of the formula (1) are structures (1) to (10) depicted below.

(1)
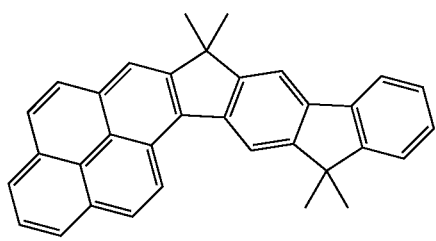

(2)
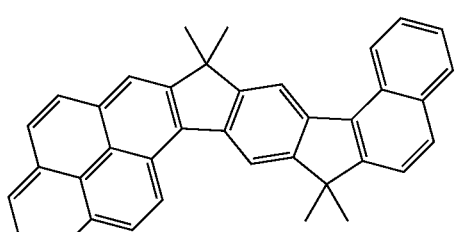

(3)
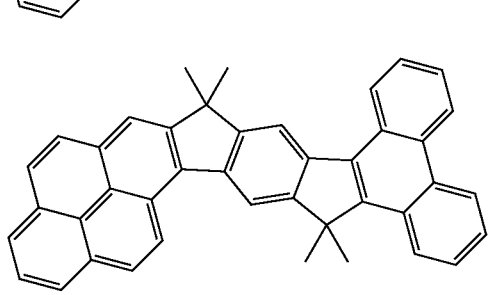

(4)
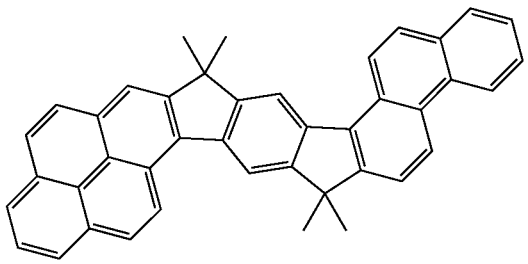

(5)
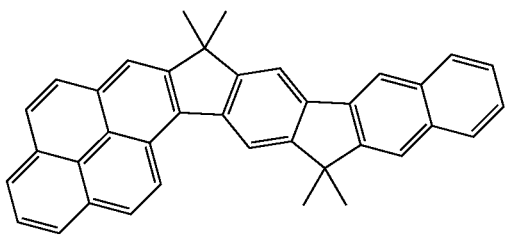

(6)
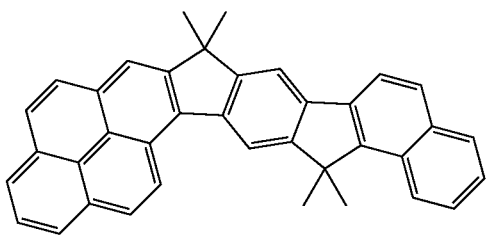

(7)
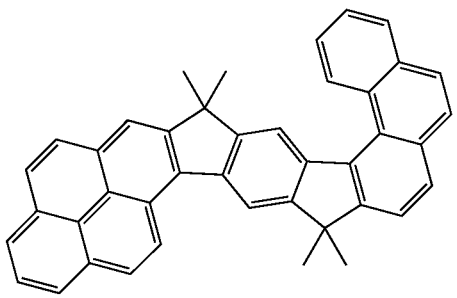

(8)
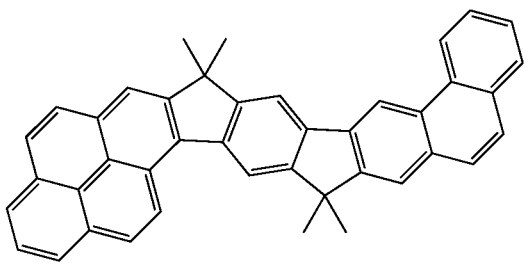

-continued (9)

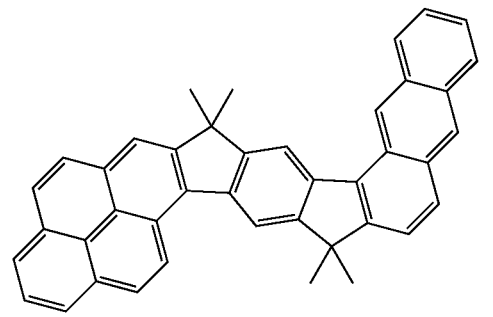

(10)

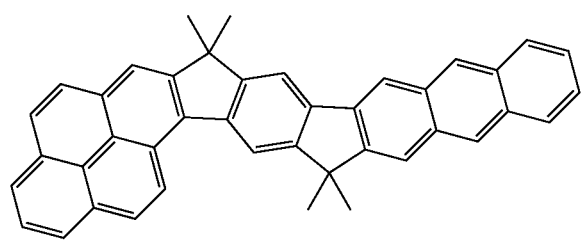

Suitable blue dopants which satisfy the above-mentioned condition for the HOMO are furthermore, for example, the following compounds:

anthracene derivatives, for example silyl-substituted anthracene derivatives or silylalkynyl-substituted anthracene derivatives (for example in accordance with T. Karatsu et al., Organic Electronics 2007, 8, 357-366), aryl-substituted anthracene derivatives (for example in accordance with Y. Kan et al., Synthetic Metals 2004, 141, 245-249) or spirobifluorene-substituted anthracene derivatives (for example in accordance with D. Gebeyehu et al., Synthetic Metals 2005, 148, 205-211).

Benzofuran derivatives, for example alkenyl-substituted benzofuran derivatives (for example in accordance with J. R. Hwu et al., Org. Lett. 2005, 7 (8), 1545-1548).

Imidazophenanthroline derivatives (for example in accordance with R.-Y. Wang et al., Adv. Funct. Mater. 2005, 15, 1483-1487).

Pyrene derivatives (for example in accordance with S. L. Tao et al., Adv. Funct. Mater. 2005, 15, 1716-1721).

Suitable host materials for the blue dopant are materials from various classes of substance. Preferred host materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/0145239). Particularly preferred host materials are selected from the classes of the oligoarylenes containing naphthalene, anthracene, benzanthracene, benzophenanthrene and/or pyrene, or atropisomers of these compounds, the ketones, the phosphine oxides and the sulfoxides. Very particularly preferred host materials are selected from the classes of the oligoarylenes containing anthracene, benzanthracene, benzophenanthrene and/or pyrene, or atropisomers of these compounds. For the purposes of this invention, an oligoarylene is intended to be taken to mean a compound in which at least three aryl or arylene groups are bonded to one another.

Preferred host materials are, in particular, selected from compounds of the formula (142)

$$Ar^4—(Ar^5)_p—Ar^6 \qquad \text{formula (142)}$$

where $Ar^4$, $Ar^5$, $Ar^6$ are on each occurrence, identically or differently, an aryl or heteroaryl group having 5 to 30 aromatic ring atoms, which may be substituted by one or more radicals $R^1$, and $R^1$ and p have the same meaning as described above; the sum of the π electrons in $Ar^4$, $Ar^5$ and $Ar^6$ here is at least 30 if p=1 and at least 36 if p=2 and at least 42 if p=3.

The group $Ar^5$ in the host materials of the formula (142) particularly preferably stands for anthracene, which may be substituted by one or more radicals $R^1$, and the groups $Ar^4$ and $Ar^6$ are preferably bonded in the 9- and 10-position. Very particularly preferably, at least one of the groups $Ar^4$ and/or $Ar^6$ is a condensed aryl group selected from 1- and 2-naphthyl, 2-, 3- and 9-phenanthrenyl and 2-, 3-, 4-, 5-, 6- and 7-benzanthracenyl, each of which may be substituted by one or more radicals $R^1$.

The preferred embodiments of the further emitting layers and of the further layers of the OLEDs are described below.

In general, all materials as used in accordance with the prior art can be used in the red- and green-emitting layers.

Preferred embodiments of the phosphorescent compound present in the phosphorescent emitter layer are described below.

Suitable phosphorescent compounds are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Particularly preferred organic electroluminescent devices comprise, as phosphorescent compound, at least one compound of the formulae (143) to (146):

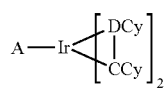

formula (143)

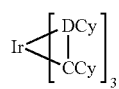

formula (144)

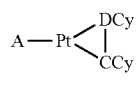

formula (145)

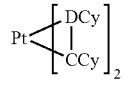

formula (146)

where $R^1$ has the same meaning as described above for formula (1), and the following applies to the other symbols used:

DCy is, identically or differently on each occurrence, a cyclic group which contains at least one donor atom, preferably nitrogen, carbon in the form of a carbene or phosphorus, via which the cyclic group is bonded to the metal, and which may in turn carry one or more substituents $R^1$; the groups DCy and CCy are connected to one another via a covalent bond;

CCy is, identically or differently on each occurrence, a cyclic group which contains a carbon atom via which the cyclic group is bonded to the metal and which may in turn carry one or more substituents $R^1$;

A is, identically or differently on each occurrence, a monoanionic, bidentate chelating ligand, preferably a diketonate ligand.

Formation of ring systems between a plurality of radicals $R^1$ means that a bridge may also be present between the groups DCy and CCy. Furthermore, formation of ring systems between a plurality of radicals $R^1$ means that a bridge may also be present between two or three ligands CCy-DCy or between one or two ligands CCy-DCy and the ligand A, giving a polydentate or polypodal ligand system respectively.

Examples of the emitters described above are revealed by the applications WO 00/70655, WO 01/41512, WO 02/02714, WO 02/15645, EP 1191613, EP 1191612, EP 1191614, WO 04/081017, WO 05/033244, WO 05/042550, WO 05/113563, WO 06/008069, WO 06/061182, WO 06/081973 and the unpublished application DE 102008027005.9. In general, all phosphorescent complexes as are used in accordance with the prior art for phosphorescent OLEDs and as are known to the person skilled in the art in the area of organic electroluminescence are suitable, and the person skilled in the art will be able to use further phosphorescent compounds without inventive step. In particular, it is known to the person skilled in the art which phosphorescent complexes emit with which emission colour.

The green-phosphorescent compound here is preferably a compound of the above-mentioned formula (144), in particular tris(phenylpyridyl)iridium, which may be substituted by one or more radicals $R^1$.

Suitable as matrix material for the phosphorescent compound are various materials as used in accordance with the prior art as matrix materials for phosphorescent compounds. Suitable matrix materials for the phosphorescent emitter are aromatic ketones, aromatic phosphine oxides or aromatic sulfoxides or sulfones, for example in accordance with WO 04/013080, WO 04/093207, WO 06/005627 or the unpublished application DE 102008033943.1, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with the unpublished application DE 102008036982.9, WO 07/063754 or WO 08/056746, zinc complexes, for example in accordance with EP 652273 or the unpublished application DE 102007053771.0, or diazasilol or tetraazasilol derivatives, for example in accordance with the unpublished application DE 102008056688.8.

It may also be advantageous to use a mixture of a hole-conducting matrix material and an electron-conducting matrix material in one or more phosphorescent emitter layers.

Apart from the cathode, anode and the emitting layers described above, the organic electroluminescent device may also comprise further layers which are not depicted in FIG. 1. These are selected, for example, from in each case one or more hole-injection layers, hole-transport layers, hole-blocking layers, electron-transport layers, electron-injection layers, electron-blocking layers, exciton-blocking layers, charge-generation layers and/or organic or inorganic p/n junctions. In addition, interlayers may also be present, in particular between a fluorescent layer and a phosphorescent layer. Furthermore, the use of more than three emitting layers may also be preferred. Furthermore, the layers, in particular the charge-transport layers, may also be doped. Doping of the layers may be advantageous for improved charge transport. However, it should be pointed out that each of these layers does not necessarily have to be present, and the choice of the layers is always also dependent on the compounds used.

The use of layers of this type is known to the person skilled in the art, and he will be able to use all materials known for layers of this type for this purpose in accordance with the prior art without inventive step.

The cathode of the electroluminescent device according to the invention is preferably made from metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). In the case of multilayered structures, further metals which have a relatively high work function, such as, for example, Ag, may also be used in addition to the said metals, in which case combinations of the metals, such as, for example, Ca/Ag or Ba/Ag, are generally used. Preference is likewise given to metal alloys, in particular alloys comprising an alkali metal or alkaline-earth metal and silver, particularly preferably an alloy of Mg and Ag. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, CsF, $Cs_2CO_3$, $BaF_2$, MgO, NaF, etc.). The layer thickness of this layer is preferably between 0.5 and 5 nm.

Preferred as anode of the electroluminescent device according to the invention are materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. At least one of the electrodes must be transparent here in order to facilitate the coupling-out of light. A preferred structure uses a transparent anode. Preferred anode materials here are conductive mixed metal oxides. Particular preference is given to indium tin oxide (ITO) or indium zinc oxide (IZO). Preference is furthermore given to conductive, doped organic materials, in particular conductive doped polymers.

The device is structured correspondingly (depending on the application), provided with contacts and finally hermetically sealed since the lifetime of devices of this type is drastically shortened in the presence of water and/or air.

In general, all further materials as employed in accordance with the prior art in organic electroluminescent devices can also be employed in combination with the blue emitter layer according to the invention in the white-emitting OLEDs.

Suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as employed in accordance with the prior art in these layers.

Examples of preferred hole-transport materials which can be used in a hole-transport or hole-injection layer in the electroluminescent device according to the invention are indenofluorenamines and derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449) or dibenzoindenofluorenamines (for example in accordance with WO 07/140847). Hole-transport and hole-injection materials which are furthermore suitable are derivatives of the compounds depicted above, as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569.

Suitable hole-transport or hole-injection materials are furthermore, for example, the materials shown in the following table.

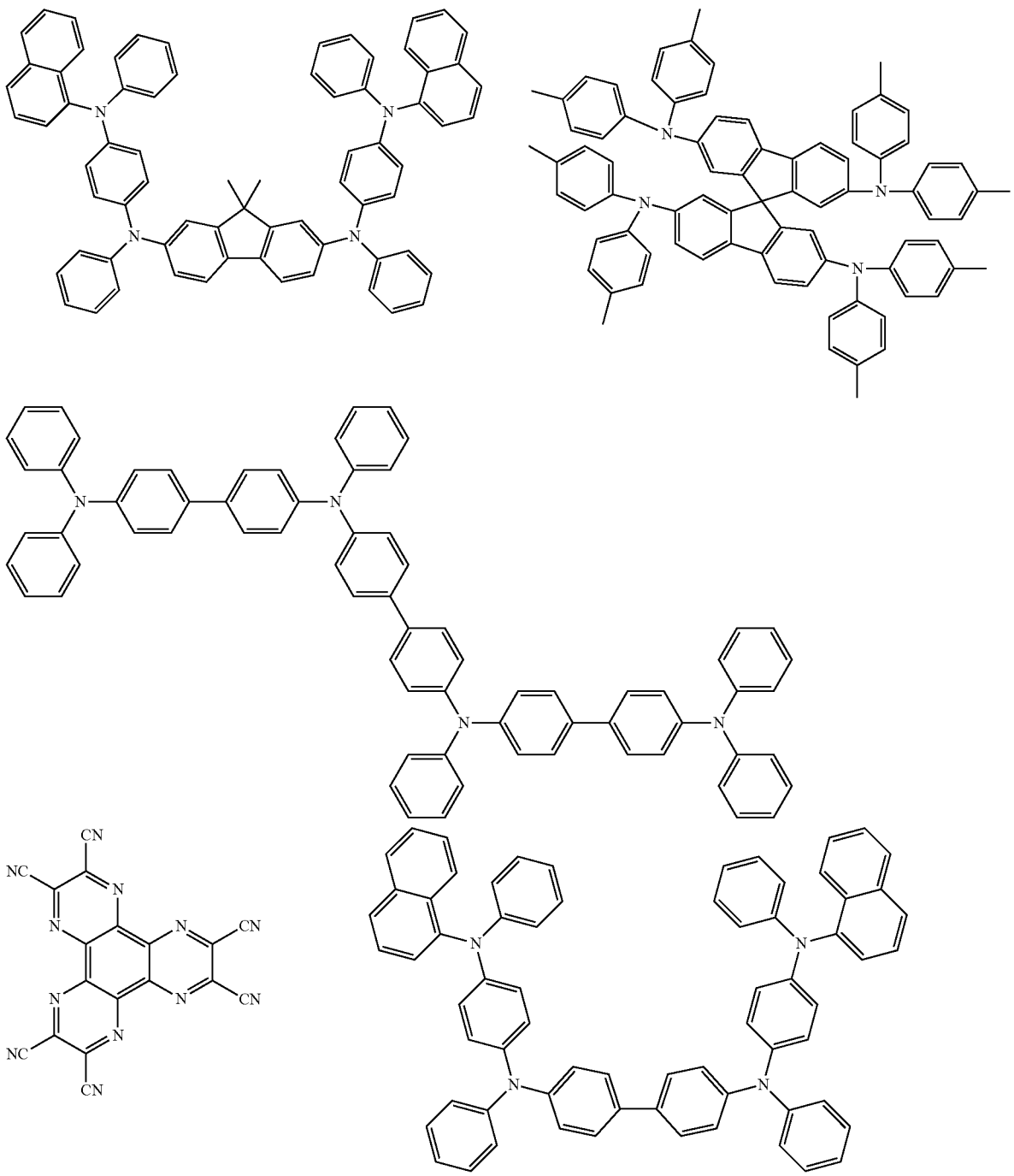

-continued
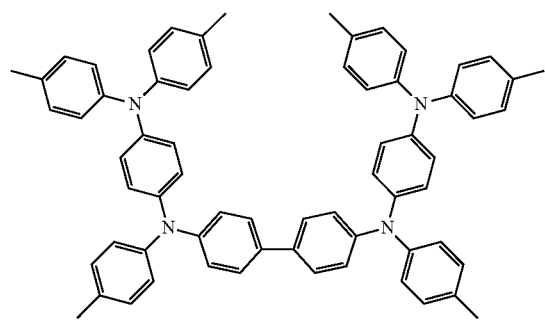
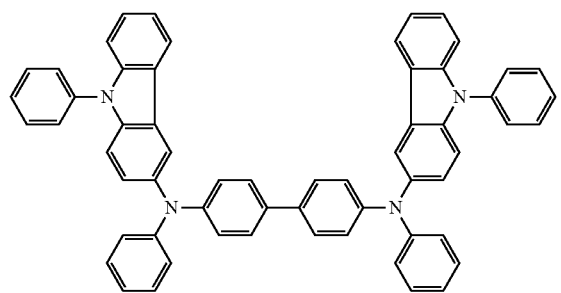
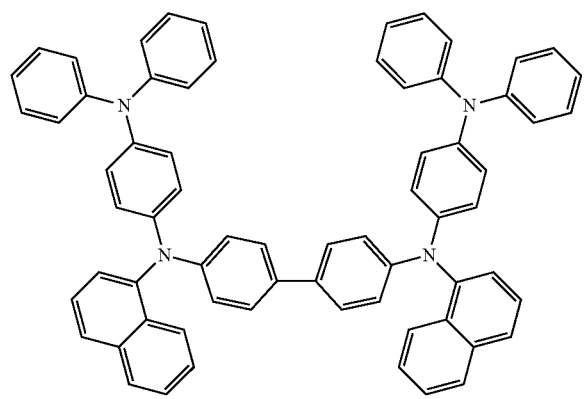
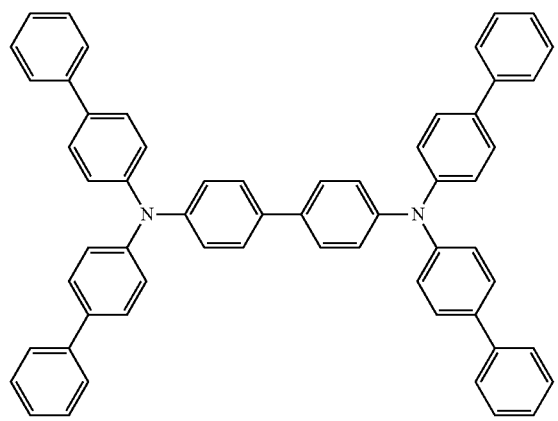
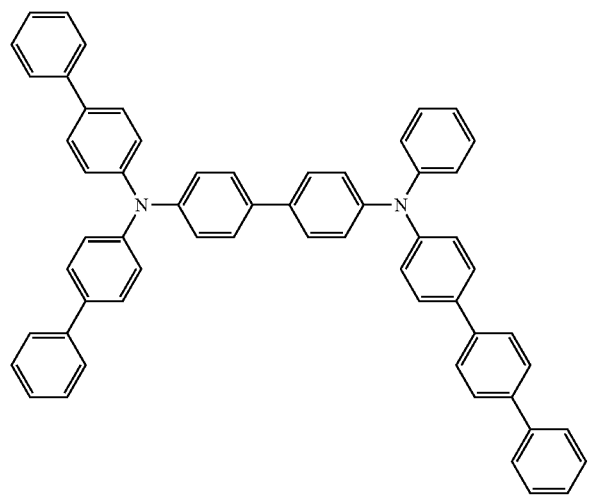
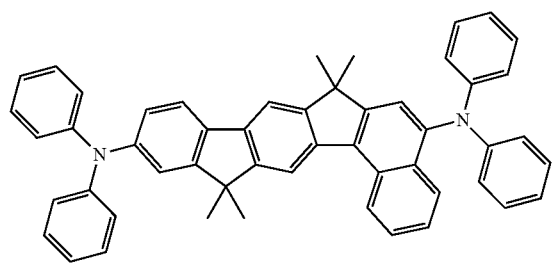
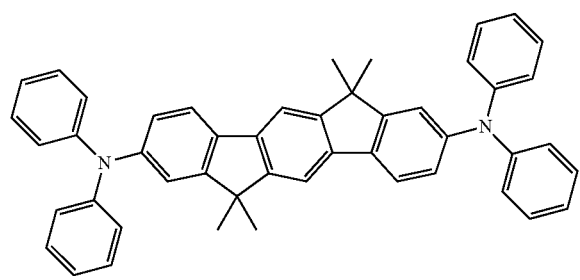
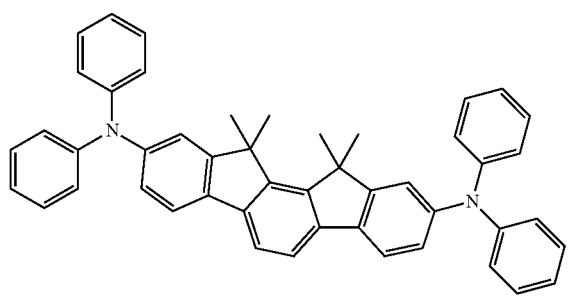

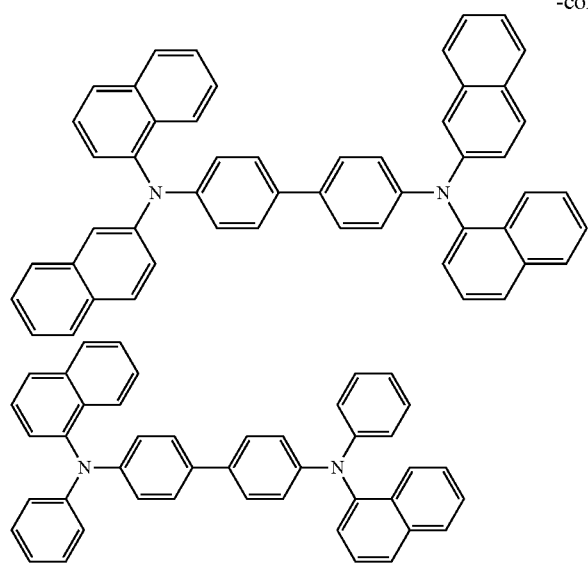

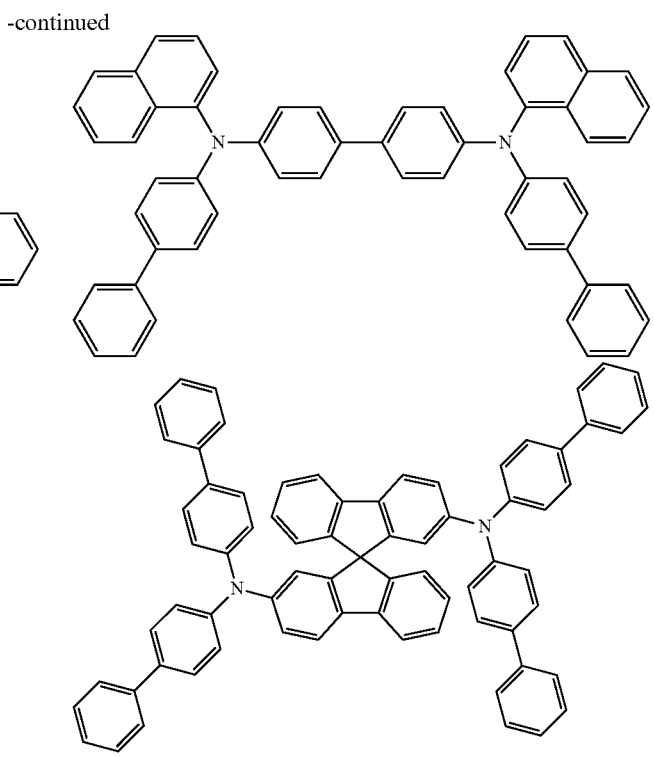

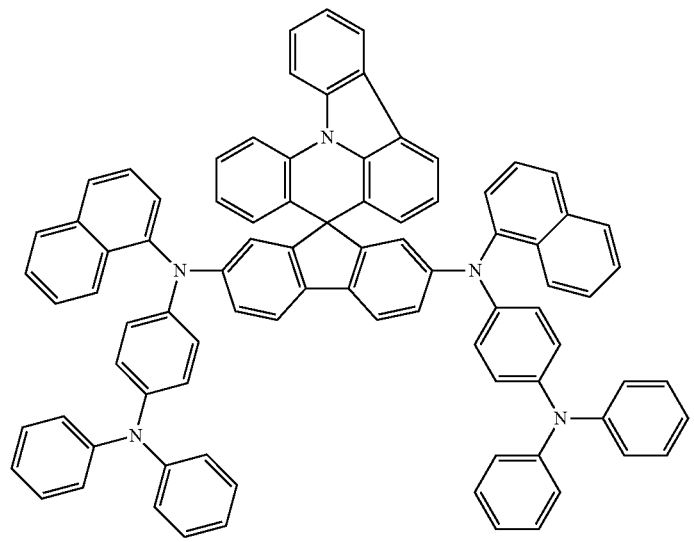 [SMILES: c1ccc(N(c2ccccc2)c2ccc(N(c3ccc4c(c3)C3(c5cc(N(c6ccc(N(c7ccccc7)c7ccccc7)cc6)c6cccc7ccccc67)ccc5-4)c4ccccc4-n4c5ccccc5c5cccc3c54)c3cccc4ccccc34)cc2)cc1]

Materials which can be used for the electron-transport layer are all materials as used in accordance with the prior art as electron-transport materials in the electron-transport layer. Aluminium complexes, for example $Alq_3$, zirconium complexes, for example $Zrq_4$, benzimidazole derivatives, triazine derivatives or aromatic ketones are particularly suitable. Suitable materials are, for example, the materials shown in the following table. Other suitable materials are derivatives of the compounds depicted above, as disclosed in JP 2000/053957, WO 03/060956, WO 04/028217 and WO 04/080975.

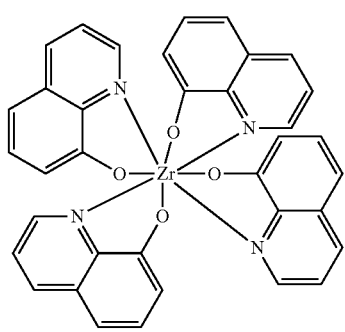

-continued

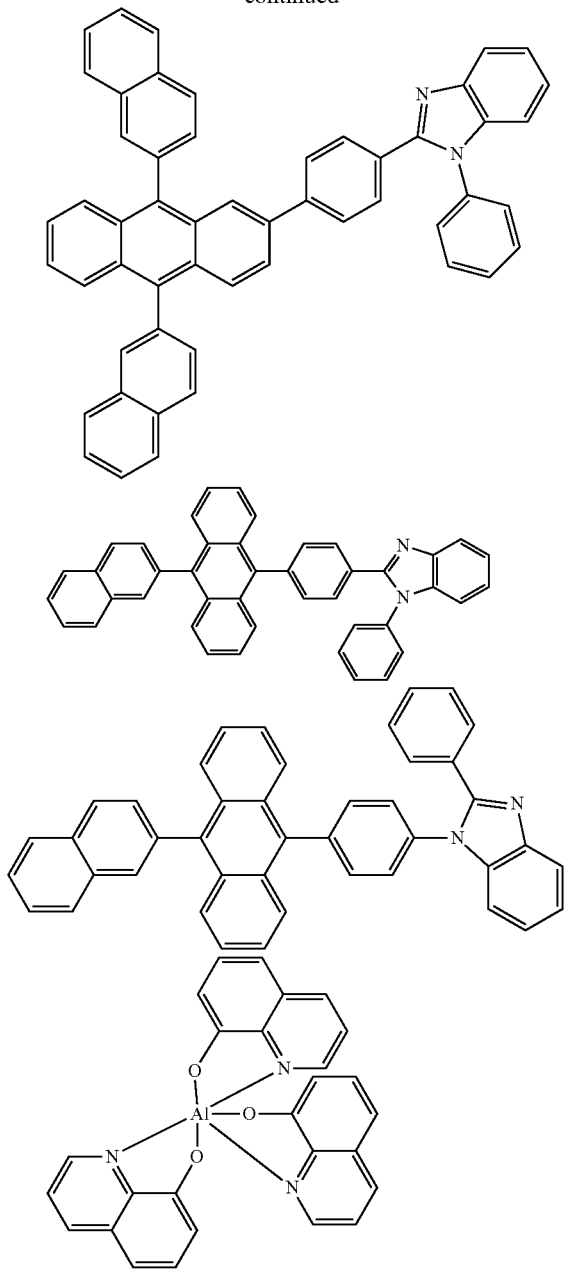

It is furthermore possible for the electron-transport layer to be doped. Suitable dopants are alkali metals or alkali metal compounds, such as, for example, Liq (lithium quinolinate). In a preferred embodiment of the invention, the electron-transport layer is doped, in particular, if the electron-transport material is a benzimidazole derivative or a triazine derivative. The preferred dopant is then Liq.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it should be noted that the pressure may also be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved by suitable substitution of the compounds. It is possible here to apply not only solutions of individual materials, but instead also solutions which comprise a plurality of compounds, for example matrix materials and dopants.

The organic electroluminescent device can also be produced by applying one or more layers from solution and vapour-depositing one or more other layers.

These processes are generally known to the person skilled in the art and can be applied by him without inventive step to the organic electroluminescent devices according to the invention.

The organic electroluminescent device according to the invention has the following surprising advantages over the prior art:

1. The organic electroluminescent device according to the invention has a very good lifetime. In particular, this lifetime is significantly improved compared with an OLED which comprises amine-containing blue-fluorescent dopants.

2. The OLED according to the invention has an improved operating voltage and power efficiency compared with an OLED which comprises amine-containing blue-fluorescent dopants.

The invention is described in greater detail by the following examples, without wishing it to be restricted thereby. The person skilled in the art, without being inventive, will be able to carry out the invention throughout the range disclosed and thus produce further organic electroluminescent devices according to the invention.

EXAMPLES

Example 1

Determination of the HOMO, LUMO and Energy Gap from Cyclic Voltammetry and Absorption Spectrum For the purposes of the present invention, the HOMO and LUMO values and the energy gap are determined by the general processes described below:

The HOMO value arises from the oxidation potential, which is measured by cyclic voltammetry (CV) at room temperature. The measuring instrument used for this purpose is an ECO Autolab system with Metrohm 663 VA stand. The working electrode is a gold electrode, the reference electrode is Ag/AgCl, the bridge electrolyte is KCl (3 mol/l) and the auxiliary electrode is platinum.

For the measurement, firstly a 0.11 M conductive-salt solution of tetrabutylammonium hexafluorophosphate ($NH_4PF_6$) in dichloromethane is prepared, introduced into the measurement cell and degassed for 5 min. Two measurement cycles are subsequently carried out with the following parameters:

Measurement technique: CV
Initial purge time: 300 s
Cleaning potential: −1 V
Cleaning time: 10 s
Deposition potential: −0.2 V
Deposition time: 10 s
Start potential: −0.2 V
End potential: 1.6 V
Voltage step: 6 mV
Sweep rate: 50 mV/s 1 ml of the sample solution (10 mg of the substance to be measured in 1 ml of dichloromethane) is subsequently added to the conductive-salt solution, and the mixture is degassed again for 5 min. Five further measurement cycles are subsequently carried out, the last three of which are recorded for evaluation. The same parameters are set as described above.

0.1 ml of ferrocene solution (100 mg of ferrocene in 1 ml of dichloromethane) is subsequently added to the solution, the mixture is degassed for 1 min, and a measurement cycle is carried out with the following parameters:

Measurement technique: CV
Initial purge time: 60 s
Cleaning potential: −1 V
Cleaning time: 10 s
Deposition potential: −0.2 V
Deposition time: 10 s
Start potential: −0.2 V
End potential: 1.6 V
Voltage step: 6 mV
Sweep rate: 50 mV/s For evaluation, the mean of the voltages of the first oxidation maximum is taken from the forward curves and the mean of the voltages of the associated reduction maximum is taken from the return curves ($V_P$ and $V_F$) for the sample solution and the solution to which ferrocene solution has been added, where the voltage used is in each case the voltage against ferrocene. The HOMO value of the substance to be investigated $E_{HOMO}$ arises as $E_{HOMO}=-[e\cdot(V_P-V_F)+4.8\ eV]$, where e represents the elementary charge.

It should be noted that appropriate modifications of the measurement method may have to be carried out in individual cases, for example if the substance to be investigated is not soluble in dichloromethane or if decomposition of the substance occurs during the measurement. If a meaningful measurement should not be possible by means of CV using the above-mentioned method, the HOMO energy will be determined by photoelectron spectroscopy by means of a model AC-2 photoelectron spectrometer from Riken Keiki Co. Ltd. (http://www.rikenkeiki.com/pages/AC2.htm), in which case it must be noted that the values obtained are typically around 0.3 eV lower than those measured by CV. For the purposes of this patent, the HOMO value is then taken to mean the value from Riken AC2+0.3 eV.

Furthermore, HOMO values lower than −6 eV cannot be measured reliably either using the CV method described or using the photoelectron spectroscopy described. In this case, the HOMO values are determined from quantum-chemical calculation by means of density functional theory (DFT). This is carried out via the commercially available Gaussian 03W (Gaussian Inc.) software using method B3PW91/6-31G (d). Standardisation of the calculated values to CV values is achieved by comparison with materials which can be measured by CV. To this end, the HOMO values of a series of materials are measured using the CV method and also calculated. The calculated values are then calibrated by means of the measured values, and this calibration factor is used for all further calculations. In this way, it is possible to calculate HOMO values which correspond very well to those which would be measured by CV. If the HOMO value of a particular substance cannot be measured by CV or Riken AC2 as described above, the HOMO value is, for the purposes of this patent, therefore taken to mean the value which is obtained in accordance with the description by a DFT calculation calibrated to CV, as described above. Examples of values calculated in this way for some common organic materials are: NPB (HOMO −5.16 eV, LUMO −2.28 eV); TCTA (HOMO −5.33 eV, LUMO −2.20 eV); TPBI (HOMO −6.26 eV, LUMO −2.48 eV). These values can be used for calibration in the calculation method.

The energy gap is determined from the absorption edge of the absorption spectrum measured on a film having a layer thickness of 50 nm. The absorption edge here is defined as the wavelength obtained when a straight line is fitted to the longest-wavelength falling flank in the absorption spectrum at its steepest point, and the value at which this straight line intersects the wavelength axis, i.e. the absorption value=0, is determined.

The LUMO value is obtained by addition of the energy gap to the HOMO value described above.

Example 2

Synthesis of 1,1-dimethylbenzindeno-1,1-dimethyl-indeno-[a]pyrene a) Diethyl 2-chloro-5-pyren-1-ylterephthalate

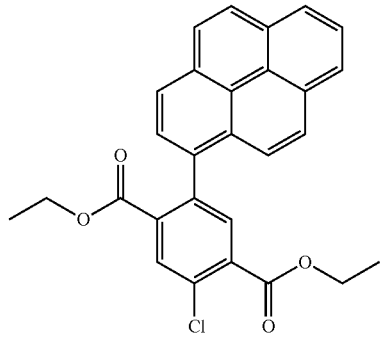 [SMILES: CCOC(=O)c1cc(-c2ccc3ccc4cccc5ccc2c3c45)c(C(=O)OCC)cc1Cl]

28.9 g (103 mmol) of bromopyrene are dissolved in 275 ml of dry THF, the solution is cooled to −75° C., and 52 ml (104 mmol) of a 2 M solution of n-butyllithium are added dropwise at this temperature. The yellow suspension is stirred at −75° C. for 1 h, and 17.5 ml (155 mmol) of trimethyl borate are then added dropwise. After warming to RT, 34.5 g (103 mmol) of diethyl chlorobromoterephthalate, 22 g (206 mmol) of $Na_2CO_3$, 1.2 g (1.03 mmol) of tetrakis(triphenylphosphine)palladium(0), 140 ml of $H_2O$, 280 ml of toluene and 140 ml of EtOH are added, and the mixture is heated at the boil for 2 h. After the organic phase has been separated off, washed twice with water and dried over $Na_2SO_4$, the solvent is removed in vacuo, and the oil remaining is brought to crystallisation in heptane. Double recrystallisation gives the product in the form of a colourless solid (33 g, 70%) having a purity of >98%, which is employed in this form in the subsequent reaction.

b) Diethyl 2-naphthalen-1-yl-5-pyren-1-ylterephthalate

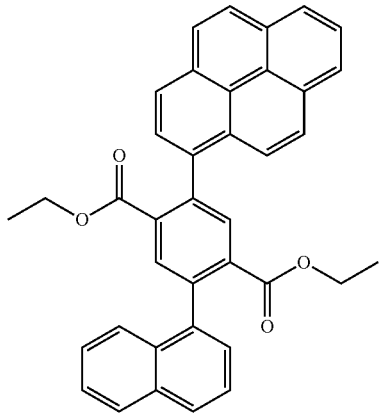 [SMILES: CCOC(=O)c1cc(-c2ccc3ccc4cccc5ccc2c3c45)c(C(=O)OCC)cc1-c1cccc2ccccc12]

43.5 g (90 mmol) of diethyl 2-chloro-5-pyren-1-ylterephthalate, 21.5 g (120 mmol) of 1-naphthylboronic acid and 58.1 g of $Cs_2CO_3$ are initially introduced in 230 ml of dry dioxane, and the mixture is saturated with $N_2$ for 30 min. 2.7 ml of a 1.0 M solution of tri-tert-butylphosphine in toluene, followed by 300 mg (1.3 mmol) of $Pd(OAc)_2$, are then added. The mixture is heated at the boil for 4 h and extended with water and EtOH, and the precipitate is filtered off with suction, washed with water and EtOH and dried. The solid is recrystallised three times from dioxane and then has, according to $^1$H-NMR, a purity of >99%. The yield is 44.2 g (90%) of colourless solid.

The following compound (Example 3b) is prepared analogously to the process described above.

c) 2-[4-(1-Hydroxy-1-methylethyl)-2-naphthalen-1-yl-5-pyren-1-yl-phenyl]propan-2-ol

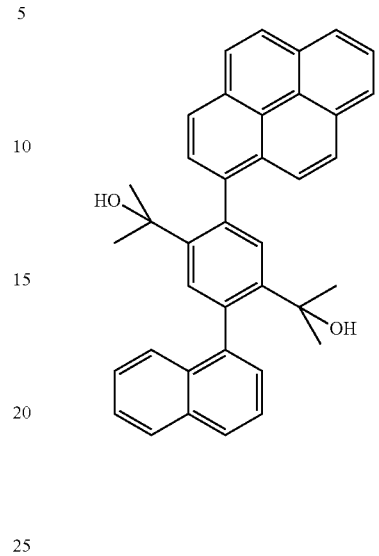

30 g (55 mol) of diethyl 2-naphthalen-1-yl-5-pyren-1-yl-terephthalate are dissolved in 270 ml of dry THF, 110 ml (330 mmol) of a 3 M methylmagnesium chloride solution in THF are added dropwise at 5° C., and the mixture is stirred at RT for 12 h. After the reaction has been interrupted by addition of 180 ml of 25% acetic acid, the mixture is worked up by extraction with ethyl acetate/water, dried over $Na_2SO_4$ and evaporated in a rotary evaporator. Recrystallisation from EtOH/toluene gives 26.3 g (92%) of colourless solid, which, according to $^1$H-NMR, has a purity of >98%.

The following compound (Example 3c) is prepared analogously to the process described above.

| Ex. | Structure | Yield (%) |
|---|---|---|
| 3b | (structure) | 67 |

| Ex. | Structure | Yield (%) |
|---|---|---|
| 3c | (structure) | 80 | d) 1,1-Dimethylbenzindeno-1,1-dimethylindeno[a]pyrene (BD1)

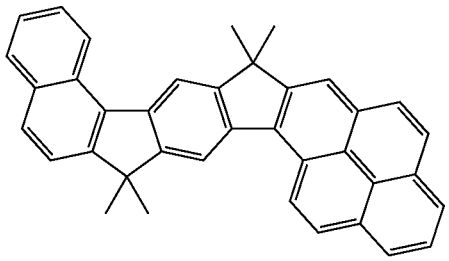 [SMILES: CC1(C)c2cc3c(cc2-c2c1ccc1ccccc21)C(C)(C)c1cc2ccc4cccc5ccc(c1-3)c2c45]

26.3 g (50.5 mmol) of 2-[4-(1-hydroxy-1-methylethyl)-2-naphthalen-1-yl-5-pyren-1-ylphenyl]propan-2-ol are dissolved in 750 ml of dichloromethane, 45 ml of methanesulfonic acid in 70 g of polyphosphoric acid are added dropwise at −20° C., and the mixture is stirred at this temperature for 1 h. When the reaction is complete, 400 ml of EtOH are added dropwise, the mixture is heated at the boil for 1 h, and the yellow solid is filtered off. Recrystallisation four times from NMP and sublimation twice in vacuo ($p=1\times10^{-5}$ mbar, T=340° C.) gives a yellow powder having a purity >99.9% (16 g, 65%).

The following compound (Example 3d, BD2) is prepared analogously to the process described above.

| Ex. | Structure | Yield (%) |
|---|---|---|
| 3d | 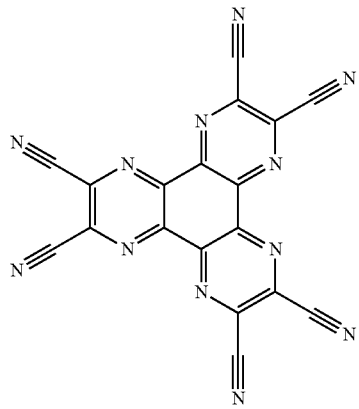 | 15 |

NPB

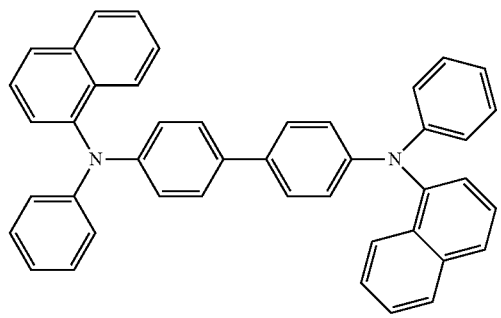

Example 4

Production of Electroluminescent Devices

Electroluminescent devices according to the invention can be produced as described, for example, in WO 05/003253.

The structures of the materials used are depicted below for clarity.

HIM

TER

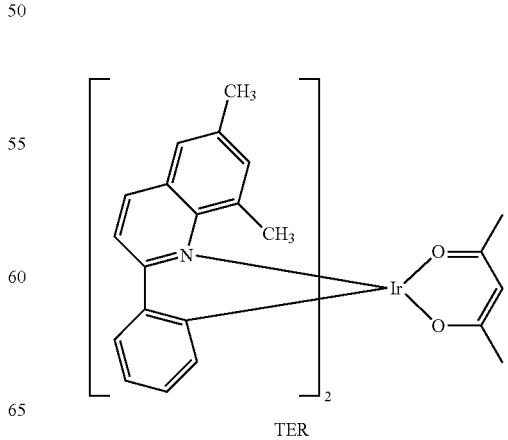

-continued
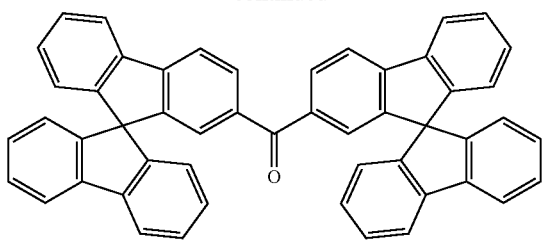
SK (WO 04/093207)
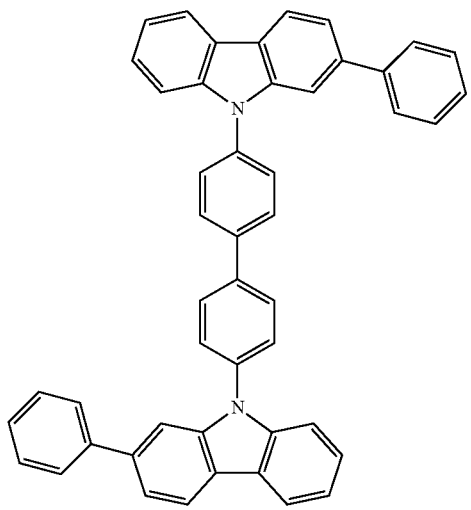
TMM (WO 08/086851)
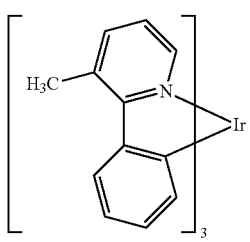
TEG
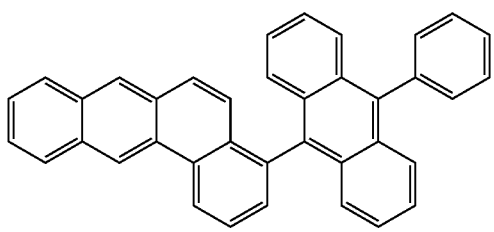
BH (WO 08/145239)
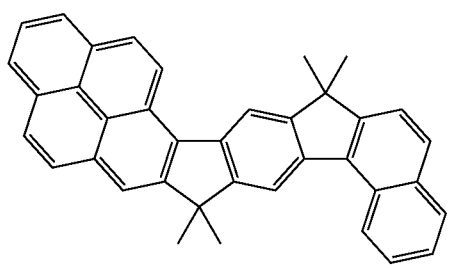
BD1
-continued
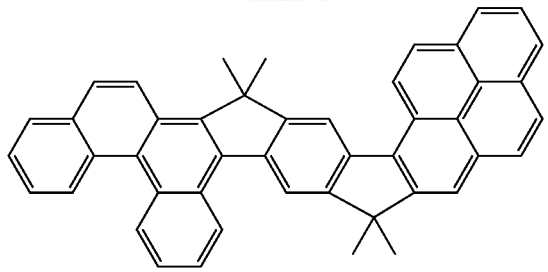
BD2
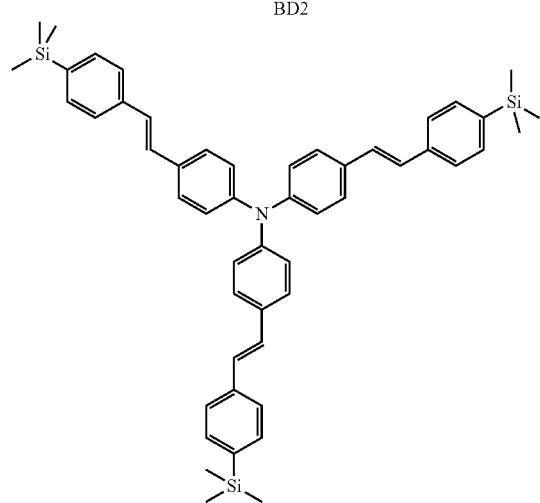
BD3 (WO 07/065549)
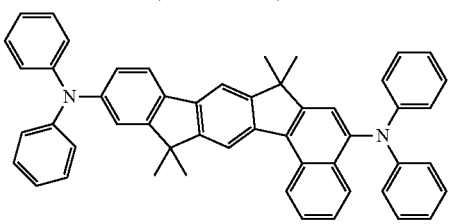
BD4 (WO 08/006449)
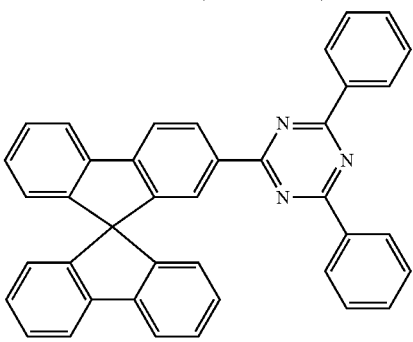
ETM
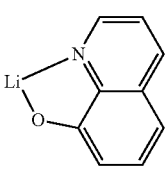
Liq These as yet unoptimised OLEDs are characterised by standard methods; for this purpose, the electroluminescence spectra and colour coordinates (in accordance with CIE 1931), the efficiency (measured in cd/A) as a function of the luminance, the operating voltage, calculated from current-voltage-luminous density characteristic lines (IUL characteristic lines), and the lifetime are determined. The results obtained are summarised in Table 1.

The results for various white OLEDs are compared below. The blue dopants here are selected so that in each case the dopant from the example according to the invention (BD1 or BD2) gives the same colour coordinates in a monochromically blue OLED as the dopant from the comparative example (BD3 or BD4). The monochrome OLED is achieved here by the following layer structure: 20 nm of HIM, 20 nm of NPB, 25 nm of BH doped with 2.5% of BD, 25 nm of ETM doped with 50% of Liq, 100 nm of Al. BD1 and BD3 here result in blue emission with colour coordinates CIE1931 0.14/0.11, BD2 and BD4 in CIE1931 0.14/0.16.

Example 5

Example 5 according to the invention is achieved by the following layer structure: 20 nm of HIM, 40 nm of NPB doped with 7% of TER, 8 nm of mixed layer consisting of 80% of TMM, 10% of SK and 10% of TEG, 25 nm of BH doped with 2.5% of BD1, 5 nm of SK, 25 nm of ETM doped with 50% of Liq, 100 nm of Al.

Example 6

Example 6 according to the invention is achieved by the following layer structure: 20 nm of HIM, 40 nm of NPB doped with 7% of TER, 8 nm of mixed layer consisting of 80% of TMM, 10% of SK and 10% of TEG, 25 nm of BH doped with 2.5% of BD2, 5 nm of SK, 25 nm of ETM doped with 50% of Liq, 100 nm of Al.

Example 7

Comparison

Comparative Example 7 is achieved by the following layer structure: 20 nm of HIM, 40 nm of NPB doped with 7% of TER, 8 nm of mixed layer consisting of 80% of TMM, 10% of SK and 10% of TEG, 25 nm of BH doped with 2.5% of BD3, 5 nm of SK, 25 nm of ETM doped with 50% of Liq, 100 nm of Al.

Example 8

Comparison

Comparative Example 8 is achieved by the following layer structure: 20 nm of HIM, 40 nm of NPB doped with 7% of TER, 8 nm of mixed layer consisting of 80% of TMM, 10% of SK and 10% of TEG, 25 nm of BH doped with 2.5% of BD4, 5 nm of SK, 25 nm of ETM doped with 50% of Liq, 100 nm of Al.

Examples 5 and 7 and Examples 6 and 8 each give rise to similar colour coordinates, meaning that the emission data can be compared well with one another. Examples 5 and 7 have bluish-white emission, Examples 6 and 8 yellowish-white emission. As described in the unpublished application DE 102008063490.5, further colour coordinates, for example CIE 0.28/0.29 or CIE 0.45/0.41, can be achieved by variation of, for example, the concentration ratios and layer thickness of the green emitter layer. The OLEDs according to the invention also have improved emission properties in this case, analogously to the examples shown, compared with the comparison of OLEDs.

Comparison of the emission data from Example 5 with Comparative Example 7 and Example 6 with Comparative Example 8 shows that the OLEDs according to the invention have both improved power efficiency and also an improved operating lifetime.

TABLE 1

| | | | Device results | | | |
|---|---|---|---|---|---|---|
| Ex. | Blue dopant | HOMO of blue dopant | Efficiency [lm/W] at 4000 cd/m² | Voltage [V] at 4000 cd/m² | CIE x/y at 4000 cd/m² | Lifetime 50% [h], initial luminance 4000 cd/m² |
| 5 | BD1 | −5.4 eV | 7.9 | 5.2 | 0.31/0.32 | 1100 |
| 6 | BD2 | −5.35 eV | 10 | 5.0 | 0.37/0.36 | 1100 |
| 7 comp. | BD3 | −5.1 eV | 7.1 | 5.5 | 0.31/0.31 | 750 |
| 8 comp. | BD4 | −5.1 eV | 9.5 | 5.2 | 0.37/0.37 | 900 |

The invention claimed is:

1. An organic electroluminescent device comprising, in this sequence, an anode, a first emitter layer, a second emitter layer which is a blue-emitting layer, where the blue-emitting layer is a fluorescent layer and comprises a host material in a proportion of 90-99.9% by vol. and a dopant in a proportion of 0.1-10% by vol., and a cathode, wherein the dopant has an HOMO of less than −5.3 eV and wherein the host material for the blue dopant is oligoarylenes, and the blue dopant is a compound of the following formula (1):

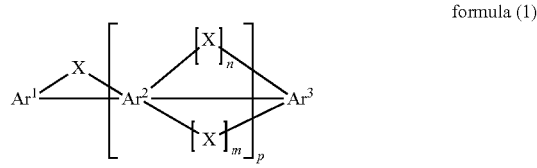

formula (1)

where the following applies to the symbols and indices used:
  $Ar^1$, $Ar^2$, $Ar^3$ are on each occurrence, identically or differently, an aryl or heteroaryl group having 6 to 22 aromatic ring atoms, which may be substituted by one or more radicals $R^1$;
  X is on each occurrence, identically or differently, a group selected from $BR^2$, $C(R^2)_2$, $Si(R^2)_2$, C=O, C=NR², C=C(R²)₂, O, S, S=O, SO₂, NR², PR², P(=O)R² or P(=S)R²;

R¹ and R² are on each occurrence, identically or differently, H, D, F, Cl, Br, I, C(=O)Ar⁴, P(=O)(Ar⁴)₂, S(=O)Ar⁴, S(=O)₂Ar⁴, CR²=CR²Ar⁴, CHO, CR³=C(R³)₂, CN, NO₂, Si(R³)₃, B(OR³)₂, B(R³)₂, B(N(R³)₂)₂, OSO₂R³, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy or thioalkoxy group having 3 to 40 C atoms, each of which may be substituted by one or more radicals R³, where in each case one or more non-adjacent CH₂ groups may be replaced by R³C=CR³, C≡C, Si(R³)₂, Ge(R³)₂, Sn(R³)₂, C=O, C=S, C=Se, C=NR³, P(=O)R³, SO, SO₂, NR³, O, S or CONR³ and where one or more H atoms may be replaced by F, Cl, Br, I, CN or NO₂, or an aromatic or heteroaromatic ring system having 5 to 60 aromatic ring atoms, which may in each case be substituted by one or more radicals R³;

R³ is on each occurrence, identically or differently, H, D or an aliphatic or aromatic hydrocarbon radical having 1 to 20 C atoms;

Ar⁴ is on each occurrence, identically or differently, an aromatic or heteroaromatic ring system having 5-30 aromatic ring atoms, which may be substituted by one or more non-aromatic radicals R¹; two radicals Ar on the same nitrogen or phosphorus atom may also be linked to one another here by a single bond or a bridge X;

in and n are 0 or 1, with the proviso that m+n=1;

p is 1;

Ar¹, Ar² and X together form a five-membered ring or a six-membered ring, and Ar², Ar³ and X together form a five-membered ring or a six-membered ring;

the sum of all π electrons in groups Ar¹, Ar² and Ar³ is at least 28 and the compound of the formula (1) contains no diarylamino group at least one of Ar¹ to Ar³ is a fused aromatic system wherein at least one of the aromatic rings is directly fused to at least three other rings.

2. The organic electroluminescent device according to claim 1, wherein the device has precisely two emitting layers, where the emitter layer on the anode side is a yellow- or orange-emitting emitter layer.

3. The organic electroluminescent device according to claim 1, wherein the device has at least three emitting layers, where one of these layers is a red- or orange-emitting emitter layer and one of the layers is a green-emitting emitter layer and the red- or orange-emitting layer is on the anode side and the green-emitting layer lies between the red-emitting layer and the blue-emitting layer.

4. The organic electroluminescent device according to claim 1, wherein the blue dopant has an HOMO (highest occupied molecular orbital) of less than −5.4 eV.

5. The organic electroluminescent device according to claim 1, wherein the blue dopant has an LUMO (lowest unoccupied molecular orbital) of less than −2.3 eV.

6. The organic electroluminescent device according to claim 1, wherein the blue dopant is present in the blue-emitting layer in a concentration of 0.2-7% by vol.

7. The organic electroluminescent device according to claim 1, wherein the symbols Ar¹, Ar² and Ar³ stand, identically or differently on each occurrence, for an aryl or heteroaryl group having 5 to 22 aromatic ring atoms.

8. The organic electroluminescent device according to claim 1, wherein the groups Ar¹ and Ar³ which form a five-membered ring with Ar² are the groups of the formulae (2) to (85) shown below, each of which may be substituted by one or more radicals R¹, and in that the groups Ar² are the groups of the formulae (86) to (110) shown below, each of which may be substituted by one or more radicals R¹; the symbol * stands for the position of the link from Ar¹ to Ar² or from Ar² to Ar³, and the symbol # stands for the position of the link to X:

formula (2)

formula (3)

formula (4)

formula (5)

formula (6)

formula (7)

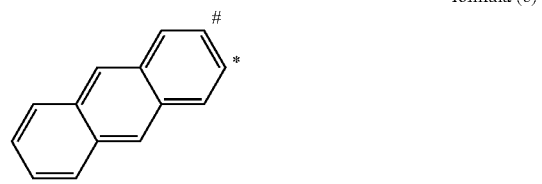

formula (8)

-continued
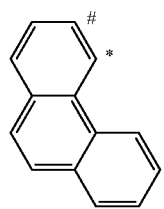
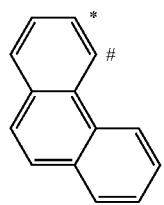
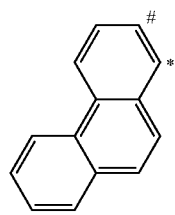
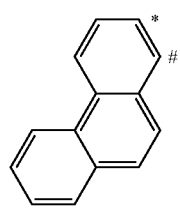
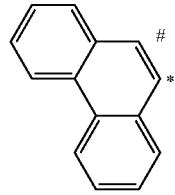
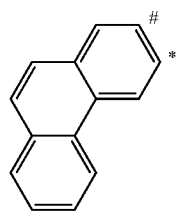
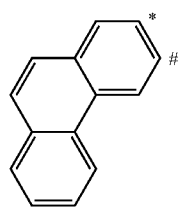
-continued
formula (9)
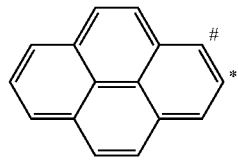
formula (10)
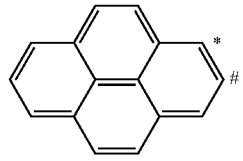
formula (11)
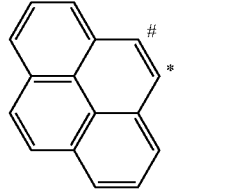
formula (12)
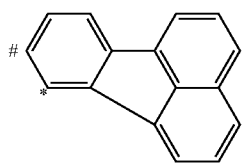
formula (13)
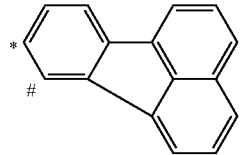
formula (14)
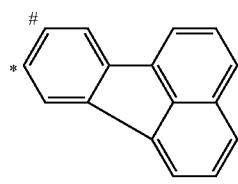
formula (15)
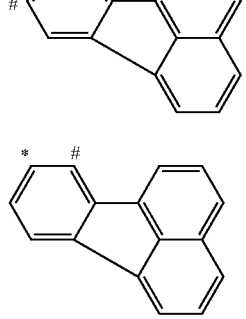
formula (16)
formula (17)
formula (18)
formula (19)
formula (20)
formula (21)
formula (22)
formula (23)
formula (24)

formula (25)
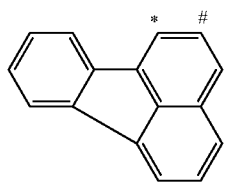
formula (26)
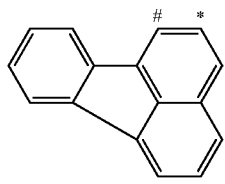
formula (27)
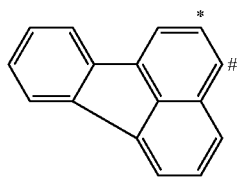
formula (28)
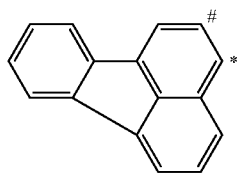
formula (29)
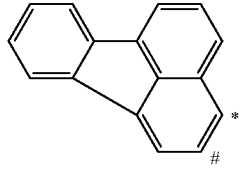
formula (30)
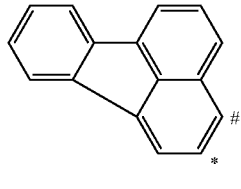
formula (31)
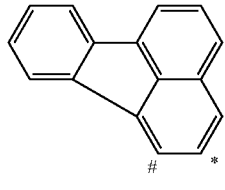
formula (32)
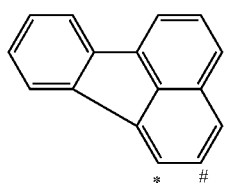
formula (33)
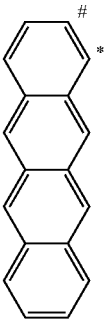
formula (34)
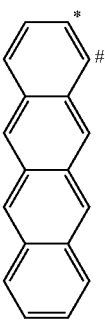
formula (35)
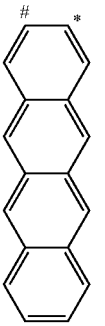
formula (36)
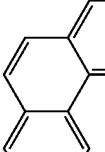
formula (37)
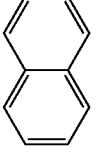

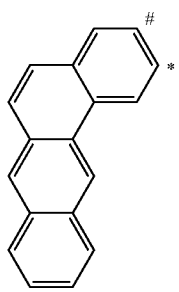
formula (38)
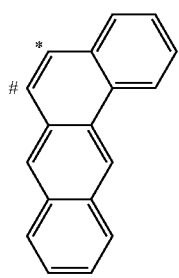
formula (43)
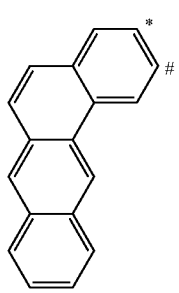
formula (39)
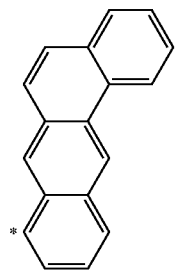
formula (44)
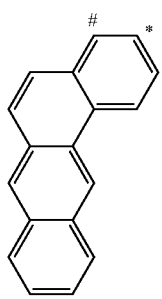
formula (40)
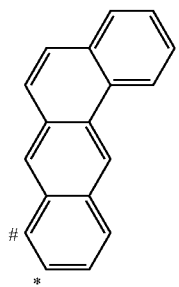
formula (45)
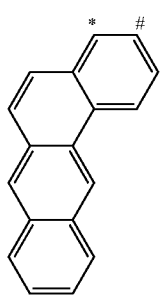
formula (41)
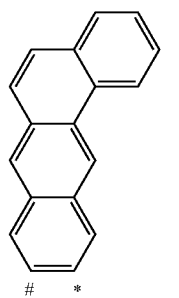
formula (46)
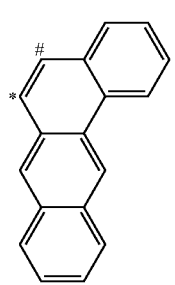
formula (42)
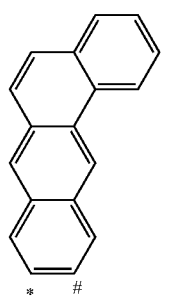
formula (47)

-continued
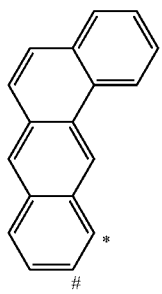
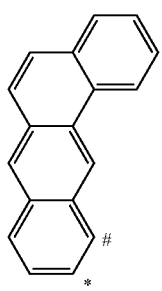
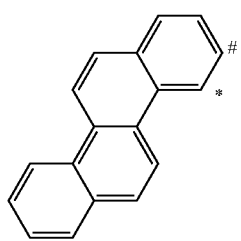
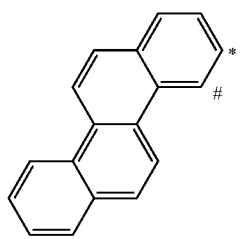
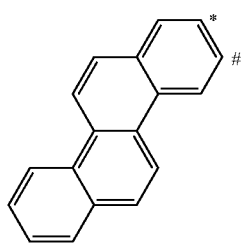
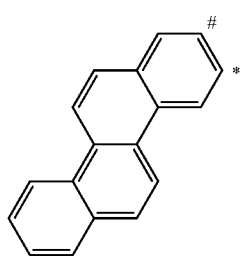
-continued
formula (48)
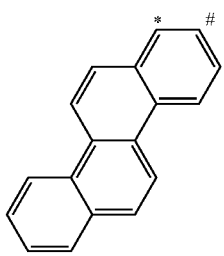
formula (49)
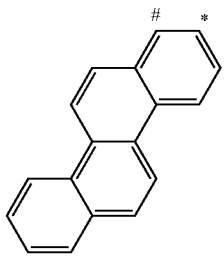
formula (50)
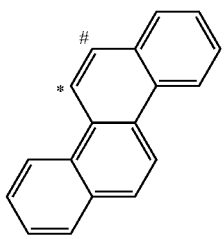
formula (51)
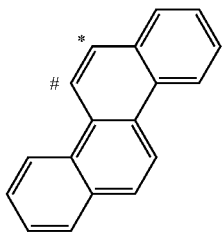
formula (52)
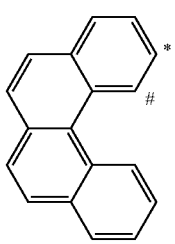
formula (53)
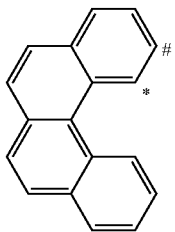
formula (54)
formula (55)
formula (56)
formula (57)
formula (58)
formula (59)

-continued
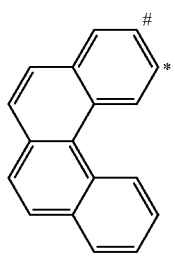
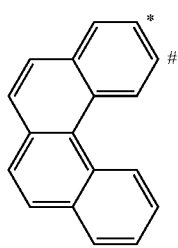
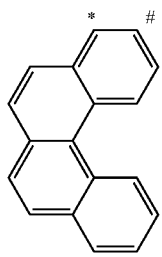
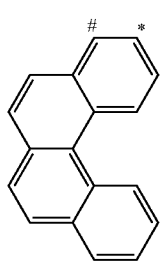
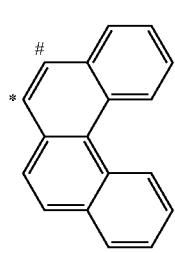
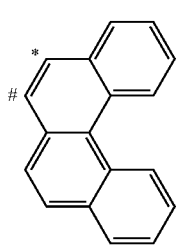
-continued
formula (60)
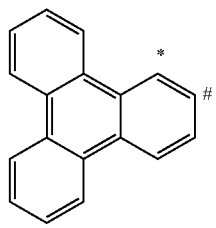
formula (61)
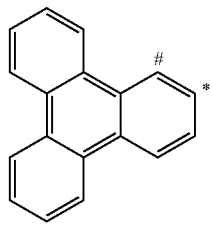
formula (62)
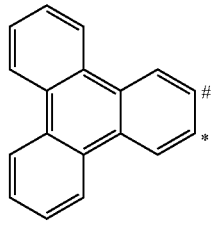
formula (63)
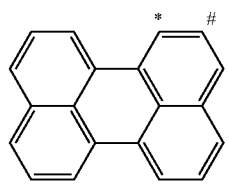
formula (64)
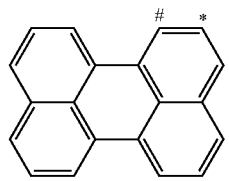
formula (65)
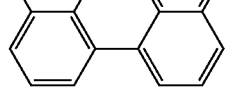
formula (66)
formula (67)
formula (68)
formula (69)
formula (70)
formula (71)
formula (72)
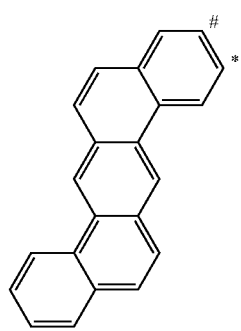

formula (73)
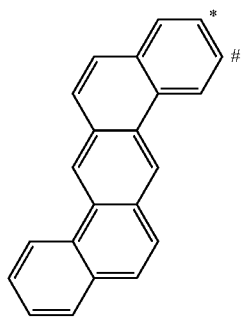
formula (74)
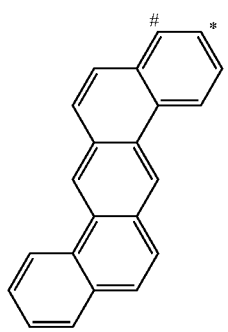
formula (75)
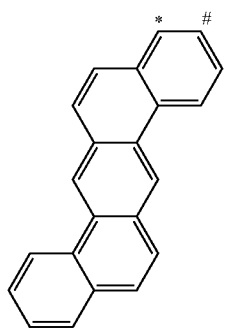
formula (76)
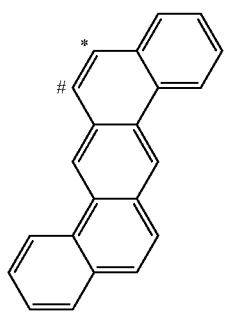
formula (77)
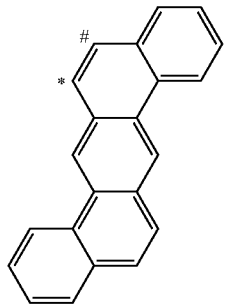
formula (78)
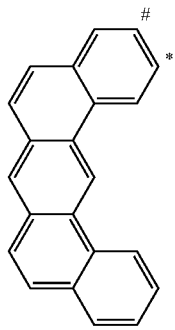
formula (79)
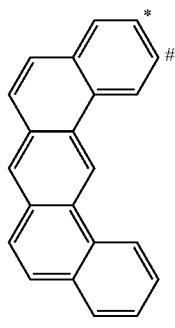
formula (80)
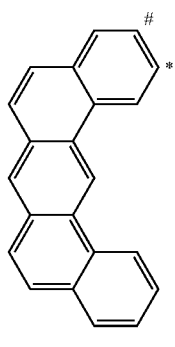
formula (81)
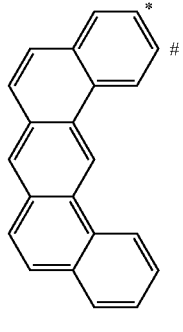
formula (82)
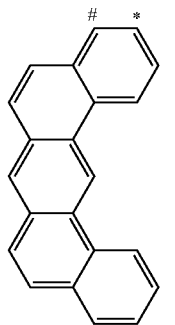

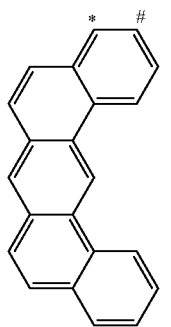
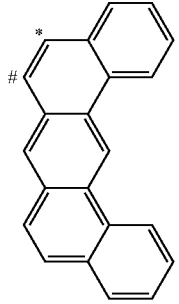
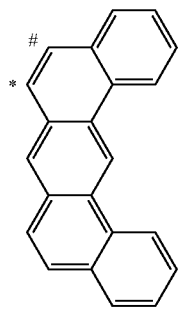
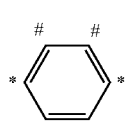
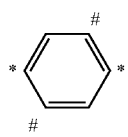
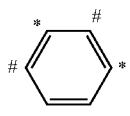
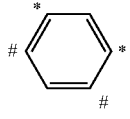
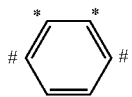
formula (83)
formula (84)
formula (85)
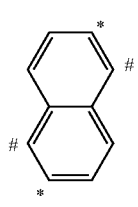
formula (86)
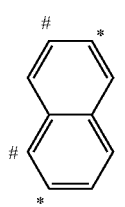
formula (87)
formula (88)
formula (89)
formula (90)
formula (91)
formula (92)
formula (93)
formula (94)
formula (95)
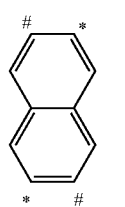
formula (96)
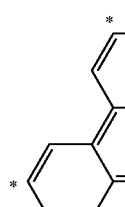
formula (97)
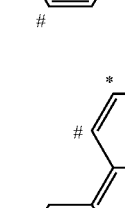

-continued
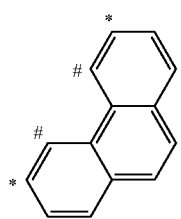
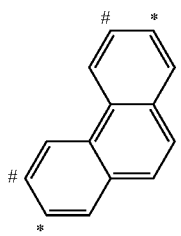
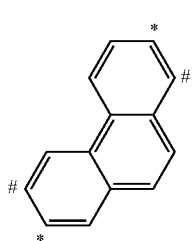
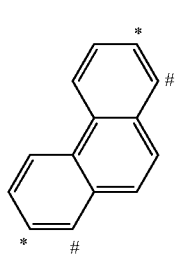
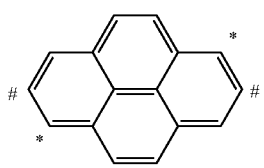
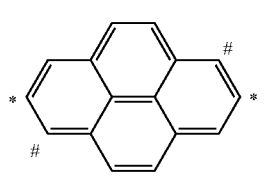
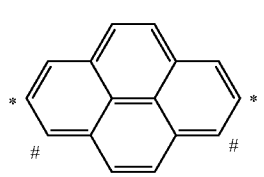
-continued
formula (98)
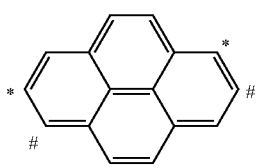
formula (99)
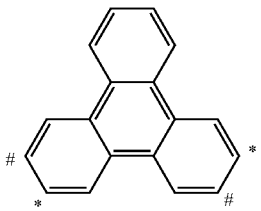
formula (100)
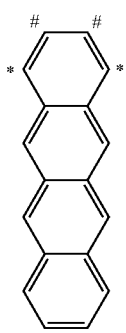
formula (101)
formula (102)
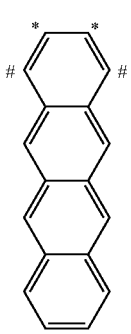
formula (103)
formula (104)
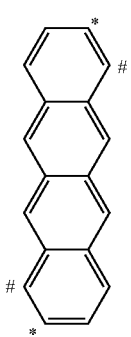
formula (105)
formula (106)
formula (107)
formula (108)
formula (109)

-continued formula (110)

9. The organic electroluminescent device according to claim 1, wherein the host material for the blue dopant is selected from compounds of the formula (142)

$$Ar^4-(Ar^5)_p-Ar^6 \qquad \text{formula (142)}$$

where $Ar^4$, $Ar^5$, $Ar^6$ are on each occurrence, identically or differently, an aryl or heteroaryl group having 5 to 30 aromatic ring atoms, which may be substituted by one or more radicals R', and R' and p is 1; the sum of the π electrons in $Ar^4$, $Ar^5$ and $Ar^6$ here is at least 30 if p=1.

10. A process for the production of the organic electroluminescent device according to claim 1, which comprises applying one or more layers by means of a sublimation process or in that one or more layers are applied by means of the OVPD (organic vapour phase deposition) process or with the aid of carrier-gas sublimation or in that one or more layers are produced from solution or by means of any desired printing process.

11. The organic electroluminescent device according to claim 1, wherein the device has precisely two emitting layers, where the emitter layer on the anode side is a phosphorescent emitter layer.

12. The organic electroluminescent device according to claim 5, wherein the blue dopant has an LUMO (lowest unoccupied molecular orbital) of less than −2.5 eV.

13. The organic electroluminescent device according to claim 6, wherein the blue dopant is present in the blue-emitting layer in a concentration of 0.8-3% by vol.

14. The organic electroluminescent device according claim 1, wherein the host material for the blue dopant is selected from the group consisting of oligoarylenes containing condensed aromatic groups.

15. The organic electroluminescent device according claim 1, wherein the host material for the blue dopant is oligoarylenes containing naphthalene, anthracene, benzanthracene, benzophenanthrene and/or pyrene.

16. The organic electroluminescent device according to claim 1, wherein the symbols $Ar^1$, $Ar^2$ and $Ar^3$ stand, identically or differently on each occurrence, for benzene, naphthalene, anthracene, phenanthrene, fluoranthene, naphthacene, benzanthracene, chrysene, pyrene, benzofluoranthene, triphenylene, perylene, dibenzanthracene, benzopyrene, picene, pentacene, pentaphene, benzophenanthrene, pyridine, pyrazine, pyrimidine, pyridazine, quinoline, isoquinoline, phenanthroline or acridine.

17. The organic electroluminescent device according to claim 3, wherein the red- or orange-emitting layer and/or the green-emitting layer are phosphorescent layers.

* * * * *